United States Patent [19]

Berger et al.

[11] 3,989,832

[45] Nov. 2, 1976

[54] COMBATING BACTERIA WITH NITROIMIDAZOLYL-TRIAZOLO-PYRIDIAZINE COMPOUNDS

[75] Inventors: Herbert Berger, Mannheim-Kafertal; Rudi Gall, Grossachsen; Kurt Stach, Mannheim-Waldhof; Wolfgang Vomel; Rita Hoffmann, both of Mannheim, all of Germany

[73] Assignee: Boehringer Mannheim G.m.b.H., Mannheim, Germany

[22] Filed: July 31, 1975

[21] Appl. No.: 600,533

Related U.S. Application Data

[62] Division of Ser. No. 336,099, Feb. 26, 1973, Pat. No. 3,928,349.

[30] Foreign Application Priority Data

Apr. 1, 1972 Germany............................ 2215999

[52] U.S. Cl................................. 424/250; 424/248
[51] Int. Cl.$^2$........................ A01N 9/00; A01N 9/22
[58] Field of Search............................ 424/248, 250

[56] References Cited
UNITED STATES PATENTS

| | | | |
|---|---|---|---|
| 3,483,193 | 12/1969 | Gall et al. | 260/240 A |
| 3,506,656 | 4/1970 | Berger et al. | 260/240 A |
| 3,686,203 | 8/1972 | Somerset et al. | 260/309 |
| 3,720,687 | 3/1973 | Kirby et al. | 260/332.5 |
| 3,721,668 | 3/1973 | Rufer et al. | 260/240 A |
| 3,723,453 | 3/1973 | Gradnik et al. | 260/309 |
| 3,790,592 | 2/1974 | Carson et al. | 260/309 |

FOREIGN PATENTS OR APPLICATIONS

| | | | |
|---|---|---|---|
| 1,187,281 | 4/1970 | United Kingdom | 260/250 AC |
| 1,123,247 | 8/1968 | United Kingdom | 260/240 A |
| 1,141,570 | 1/1969 | United Kingdom | 260/250 AC |

*Primary Examiner*—James O. Thomas, Jr.
*Assistant Examiner*—Allen J. Robinson
*Attorney, Agent, or Firm*—Burgess, Dinklage & Sprung

[57] ABSTRACT

Nitroimidazolyl-s-triazolo[4,3-b]pyridazines of the formula:

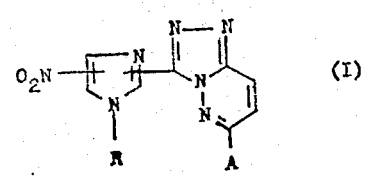

wherein R is hydrogen or lower alkyl optionally substituted in the 2-position by hydroxyl or by lower acyloxy or lower alkoxy;

A is hydrogen, halogen, azido, cyano; lower alkyl, alkoxy, alkylthio, alkylsulfonyl, carboxyl; lower alkoxycarbonyl, lower alkoxycarbonimidoyl; or hydrazino, carbamoyl, amidino or a carboximidohydrazide group optionally substituted by one or two lower acyl, alkyl or cycloalkyl radicals; or A is a radical of the formula:

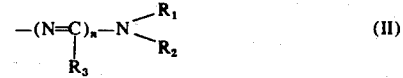

wherein $R_1$ and $R_2$ are, individually, hydrogen or a number of organic radicals or, taken together, can be an alkylene bridge; and $R_3$ is hydrogen or lower alkyl; or, together with $R_2$, $R_3$ can form an alkylene bridge;

$n$ is 0 or 1;

and the pharmaceutically compatible thereof, possess high in vivo effectiveness as antimicrobials.

15 Claims, No Drawings

COMBATING BACTERIA WITH NITROIMIDAZOLYL-TRIAZOLO-PYRIDIAZINE COMPOUNDS

This is a division of application Ser. No. 336,099, filed Feb. 26, 1973, now U.S. Pat. No. 3,928,349 issued Dec. 23, 1975.

The present invention is concerned with new nitroimidazolyl-triazolo-pyridazine compounds, with therapeutic, particularly antimicrobial, compositions containing them, and with the application of such compounds as antimicrobials.

Many anti-microbially-active nitroimidazoles have been described in the literature which are mainly effective as agents against *Protozoa*, for example *Trichomonades* and *Salmonellae* (cf., for example, German patent specification No. 1,920,635).

We have now found a hitherto unknown class of nitroimidazoles which, surprisingly, not only exhibit a high anti-microbial activity in vitro but also have an unexpectedly high effectiveness in vivo, not only in the urine but also systemically.

Thus, according to the present invention, there are provided nitroimidazolyl-s-triazolo[4,3-b]pyridazines of the general formula:

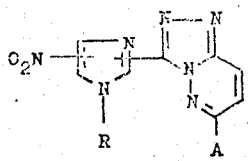

wherein R is hydrogen or lower alkyl optionally substituted in the 2-position by hydroxyl or by lower acyloxy or lower alkoxy; A is hydrogen, halogen, azido, cyano; lower alkyl, alkoxy, alkylthio, alkylsulfonyl, carboxyl; lower alkoxycarbonyl, lower alkoxycarbonimidoyl; or hydrazino, carbamoyl, amidino or a carboximidohydrazide group optionally substituted by one or two lower acyl(i.e., alkanoyl), alkyl or cycloalkyl radicals; or A is a radical of the general formula:

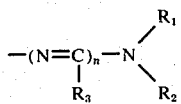

wherein $R_1$ and $R_2$, which may be the same or different, are hydrogen or lower acyl (i.e. alkanoyl, aroyl), alkoxycarbonyl or straight-chained, branched or cyclic alkyl radicals, which optionally contain a hydroxyl, alkoxy or amino group, which latter can, in turn, also be substituted by one or two alkyl or acyl (i.e., alkanoyl) radicals, or $R_1$ and $R_2$ can together represent an alkylene bridge containing from 3 to 6 carbon atoms which can be interrupted by an oxygen or sulfur atom or by a nitrogen atom which bears either a hydrogen atom or a lower alkyl radical and which alkylene bridge can be substituted by hydroxyl or alkyl or $R_1$ and $R_2$, together, are lower dialkylsulfimino or dialkylsulfoximino $R_3$ is hydrogen or lower alkyl; or $R_3$, together with $R_2$, can form an alkylene bridge containing from 3 to 4 carbon atoms; and $n$ is 0 or 1; and the pharmaceutically compatible salts thereof.

According to the present invention, the straight-chained and branched alkyl radicals can be of from 1 to 6 and preferably 1 to 4 carbon atoms and the cyclic alkyl radicals can contain 3 to 8 and, preferably, 5 to 6 ring carbon atoms. The same also applies to other radicals which contain alkyl groups.

The new compounds (I) according to the present invention can be prepared, for example, by one of the following methods:

a. when A is a radical of general formula (II), a compound of the general formula:

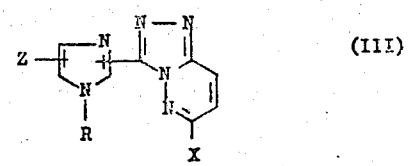

wherein X is a reactive group, Z is a nitro or amino group and R has the same meaning as above, is reacted with an amine or with an amine derivative, whereafter, if necessary, a substituent is introduced into, split off from or changed in the amino group; or b. a compound of the general formula:

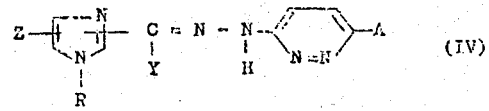

wherein R, Z and A have the same meanings as above and Y is a hydrogen atom or a hydroxyl or amino group, is cyclized and, if necessary, a substituent A subsequently converted into a different substituent A, as defined above, and, when Z is an amino group, this is converted into a nitro group and, if desired, the compound obtained is converted into a pharmacologically compatible salt.

As reactive compounds of general formula (III), there are preferably used reactive esters, for example, halides (especially chlorides), azides and imido esters (which are preferably prepared from an appropriate amine and an ortho ester, for example, an orthoformic ester or orthoacetic ester), sulfonic acid esters (for example tosylates or mesylates) or also the methylsulphonyl compounds.

Examples of amines which can be used in process a) include ammonia, methylamine, ethylamine, isopropylamine, cyclohexylamine, 4-hydroxycyclohexylamine, 4-methylcyclohexylamine, 2-hydroxyethylamine, bis-(2-hydroxyethyl)-amine, 2-methoxyethylamine, 2-hydroxyisopropylamine, dimethylamine, diethylamine, methylethylamine, N-acetylethylenediamine, N-methylethylenediamine, cyclic amines, such as piperidine, 4-hydroxypiperidine, 4-methylpiperidine, piperazine, 4-methylpiperazine, morpholine and thiamorpholine.

As amine derivatives, there can be used acylamines, for example, dimethylformamide, diethylformamide, dimethylacetamide, diethylacetamide, N-formylmorpholine, N-acetylmorpholine, N-formylthiamorpholine, N-acetylthiamorpholine, 1-formyl-4-methylpiperazine, 1-acetyl-4-methylpiperazine, 1-formylpiperidine, 1-acetylpiperidine, N-methyl-2-pyrrolidone, N- methyl-2-piperidone, potassium phthalimide or hydrazine.

The reaction of the compounds of general formula (III), with the amines preferably takes place at ambient temperature or at an elevated temperature in a polar solvent, for example, dioxan or a lower alcohol, possibly in admixture with water, or in an excess of the amine used for the reaction. For the removal of liberated acid, it can be advantageous to add a base, for example, sodium carbonate or a tertiary amine.

A primary amine group can be introduced, for example, either by reaction with ammonia or by reaction with potassium phthalimide, preferably in dimethylsulphoxide, at an elevated temperature and subsequent hydrolysis of the phthalimido compound with an aqueous mineral acid or with hydrazine. From the amine thus obtained, by reaction with an adduct of phosphorus oxychloride and an acyl compound of a secondary amine or by reaction with an acetal of such an acyl compound, there is obtained the corresponding amidine. The reaction is preferably carried out in an inert solvent, for example in dioxan, at a slightly elevated temperature. By reaction with dialkylsulphoxides in the presence of acid chlorides, also preferably at a slightly elevated temperature, there can be obtained the corresponding sulphimino compounds. The sulphoximino compounds are preferably prepared by reacting compounds of general formula (III), in which X is an azido group, with dimethylsulphoxide at boiling temperature. The alkoxycarbonylamino compounds of general formula (I) can be obtained, for example, by reacting an appropriate amine with phosgene to give the corresponding carbamic acid chloride, followed by thermal decomposition to the isocyanate and subsequent reaction thereof with an appropriate alcohol or by reaction with an appropriate chloroformic acid ester.

When Y represents a hydrogen atom, compounds of general formula (IV) can be oxidatively cyclized, for example, with lead tetraacetate in acetic acid or trifluoroacetic acid. When Y represents a hydroxyl group, cyclization can take place by splitting off water either thermally or with a strong water-splitting agent. When Y is an amino group, cyclization can be carried out by splitting off ammonia thermally or by the addition of a strong acid. The above reactions can be promoted by the addition of inert solvents.

In the case of the subsequent alteration of a substituent A, for example, a halogen atom or an alkoxy, alkylthio or alkylsulfonyl radical can be converted into a hydrazino or azido group or a halogen atom can be replaced by an alkoxy, alkylthio or alkylsulfonyl radical. The reactions are preferably carried out at ambient temperature or at an elevated temperature in polar solvents or mixtures thereof. The reaction components are preferably used in an activated form, for example, as alcoholates, thioalcoholates, azides or sulfinates. Conversion of nitriles into carboxylic acid esters can be carried out by heating with alcoholic hydrochloric acid under reflux. For conversion into free carboxylic acids, the appropriate esters can be hydrolyzed with, for example, 90%-aqueous formic acid and methane-sulfonic acid at an elevated temperature. Carboxylic acids can be converted into carboxylic acid chlorides, for example, by reaction with thionyl chloride. These can then be reacted at ambient temperature with aqueous amines to give the corresponding carbonamides. In the same way, nitriles can be converted into the corresponding imido esters via the imide chlorides or with the calculated amount of an alcohol and excess dry gaseous hydrogen chloride in organic solvents at temperatures from 0° C up to a slightly elevated temperature. These imido esters can then be reacted with amines or hydrazines to give carbimic acid amides or carbimic acid hydrazides, respectively.

When Z is an amino group, this can be subsequently converted into a nitro group, for example, by oxidation with hydrogen peroxide in sulfuric acid or by a Sandmeyer reaction of the corresponding diazonium salt with sodium nitrite.

Preferred compounds according to the present invention are, in addition to those mentioned in the specific Examples, the following:

1. 3-(5-nitro-1-methyl-2-imidazolyl)-6-cyclohexylamino-s-triazolo[4,3-b]pyridazine;
2. 3-(5-nitro-1-methyl-2-imidazolyl)-6-(4-hydroxycyclohexylamino)-s-triazolo[4,3-b]pyridazine;
3. 3-(5-nitro-1-methyl-2-imidazolyl)-6-(4-methylcyclohexylamino)-s-trizolo[4,3-b]pyridazine;
4. 3-(5-nitro-1-methyl-2-imidazolyl)-6-(β-methoxyethylamino)-s-triazolo[4,3-b]pyridazine;
5. 3-(5-nitro-1-methyl-2-imidazolyl)-6-(2-hydroxyisopropylamino)-s-triazolo[4,3-b]pyridazine;
6. 3-(5-nitro-1-methyl-2-imidazolyl)-6-(2-methoxyisopropylamino)-s-triazolo[4,3-b]pyridazine;
7. 3-(5-nitro-1-methyl-2-imidazolyl)-6-ethoxycarbonylamino-s-triazolo[4,3-b]pyridazine;
8. 3-(5-nitro-1-methyl-2-imidazolyl)-6-[β-(dimethylamino)-ethylamino]-s-triazolo[4,3-b]pyridazine;
9. 3-(5-nitro-1-methyl-2-imidazolyl)-6-[N-methyl-N-(β-dimethylamino-ethyl)-amino]-s-triazolo[4,3-b]pyridazine;
10. 3-(5-nitro-1-methyl-2-imidazolyl)-6-[N-methyl-N-(β-hydroxyethylamino]-s-triazolo[4,3-b]pyridazine;
11. 3-(5-nitro-1-methyl-2-imidazolyl)-6-[β-(acetylamino)-ethylamino]-s-triazolo[4,3-b]pyridazine;
12. 3-(5-nitro-1-methyl-2-imidazolyl)-6-thiamorpholino-s-triazolo[4,3-b]pyridazine;
13. 3-(5-nitro-1-methyl-2-imidazolyl)-6-cyclopropylamino-s-triazolo[4,3-b]pyridazine;
14. 3-(5-nitro-1-methyl-2-imidazolyl)-6-cyclopropylamino-methylene-amino-s-triazolo[4,3-b]pyridazine;
15. 3-(5-nitro-1-methyl-2-imidazolyl)-6-(4-hydroxycyclo-hexylamino-methyleneamino)-s-triazolo[4,3-b]pyridazine;
16. 3-(5-nitro-1-methyl-2-imidazolyl)-6-(1-cyclohexylamino-ethylideneamino)-s-triazolo[4,3-b]pyridazine;
17. 3-(5-nitro-1-methyl-2-imidazolyl)-6-[1-(4-methyl-1-piperazinyl)-ethylideneamino]-s-triazolo[4,3-b]-pyridazine;
18. 3-(5-nitro-1-methyl-2-imidazolyl)-6-(1-morpholino-ethylideneamino)-s-triazolo[4,3-b]pyridazine;
19. 3-(5-nitro-1-methyl-2-imidazolyl)-6-[1-thiamorpholino-ethylideneamino]-s-triazolo[4,3-b]pyridazine;
20. 3-(5-nitro-1-methyl-2-imidazolyl)-6-(1-cyclopropylamino-ethylideneamino)-s-triazolo[4,3-b]pyridazine;
21. 3-(5-nitro-1-methyl-2-imidazolyl)-6-(1-methylamino-ethylideneamino)-s-triazolo[4,3-b]pyridazine;

22. 3-(5-nitro-1-methyl-2-imidazolyl)-6-[1-(4-hydroxycyclohexylamino)-ethylideneamino]-s-triazolo[4,3-b]-pyridazine;
23. 3-(5-nitro-1-methyl-2-imidazolyl)-6-[1-(4-hydroxy-piperidino)-ethylideneamino]-s-triazolo[4,3-b]-pyridazine;
24. 3-(5-nitro-1-methyl-2-imidazolyl)-6-[1-(4-methyl-piperidino)-ethylideneamino]-s-triazolo[4,3-b]-pyridazine;
25. 3-(5-nitro-1-methyl-2-imidazolyl)-6-[1-(β-dimethylamino-ethylamino)-ethylideneamino]-s-triazolo[4.3-b]-pyridazine;
26. 3-(5-nitro-1-methyl-2-imidazolyl)-6-[1-(β-hydroxyethyl-amino)-ethylideneamino]-s-triazolo[4,3-b]pyridazine;
27. 3-(5-nitro-1-methyl-2-imidazolyl)-6-methylthio-s-triazolo[4,3-b]pyridazine;
28. 3-(5-nitro-1-methyl-2-imidazolyl)-s-triazolo[4,3-b]-pyridazine-6-carbimic acid methyl ester;
29. 3-(5-nitro-1-methyl-2-imidazolyl)-6-amidino-s-triazolo-[4,3-b]pyridazine;
30. 3-(5-nitro-1-methyl-2-imidazolyl)-6-($N^1$-methylamidino)-s-triazolo[4,3-b]pyridazine;
31. 3-(5-nitro-1-methyl-2-imidazolyl)-6-cyclohexyl-carbamoyl-s-triazolo[4,3-b]pyridazine;
32. 3-(5-nitro-1-methyl-2-imidazolyl)-s-triazolo[4,3-b]-pyridazine-6-carbimide hydrazide;
33. 3-(5-nitro-1-methyl-2-imidazolyl)-6-(N,N-dimethylamidino)-s-triazolo[4,3-b]pyridazine;
34. 3-(5-nitro-1-methyl-2-imidazolyl)-s-triazolo[4,3-b]-pyridazine-6-carboximic acid morpholide;
35. 3-(5-nitro-1-methyl-2-imidazolyl)-6-methyl-s-triazolo-[4,3-b]pyridazine;
36. 3-(1-methyl-2-nitro-5-imidazolyl)-6-azido-s-triazolo-[4,3-b]pyridazine;
37. 3-(1-methyl-2-nitro-5-imidazolyl)-6-methoxy-s-triazolo-[4,3-b]pyridazine;
38. 3-(1-methyl-2-nitro-5-imidazolyl)-6-methylsulphonyl-s-triazolo[4,3-b]pyridazine;
39. 3-(1-methyl-2-nitro-5-imidazolyl)-6-carboxy-s-triazolo-[4,3-b]pyridazine;
40. 3-(1-methyl-2-nitro-5-imidazolyl)-6-methoxycarbonylamino-s-triazolo[4,3-b]pyridazine;
41. 3-(1-methyl-2-nitro-5-imidazolyl)-6-hydrazino-s-triazolo[4,3-b]pyridazine;
42. 3-(1-methyl-2-nitro-5-imidazolyl)-6-carbamoyl-s-triazolo[4,3-b]pyridazine;
43. 3-(1-methyl-2-nitro-5-imidazolyl)-6-amidino-s-triazolo-[4,3-b]pyridazine;
44. 3-(1-methyl-2-nitro-5-imidazolyl)-6-cyclopropylamino-s-triazolo[4,3-b]pyridazine;
45. 3-(1-methyl-2-nitro-5-imidazolyl)-6-cyclohexylamino-s-triazolo[4,3-b]pyridazine;
46. 3-(1-methyl-2-nitro-5-imidazolyl)-6-(β-hydroxyethyl-amino)-s-triazolo[4,3-b]pyridazine;
47. 3-(1-methyl-2-nitro-5-imidazolyl)-6-(β-methoxyethyl-amino)-s-triazolo[4,3-b]pyridazine;
48. 3-(1-methyl-2-nitro-5-imidazolyl)-6-(β-acetylaminoethyl-amino)-s-triazolo[4,3-b]pyridazine;
49. 3-(1-methyl-2-nitro-5-imidazolyl)-6-thiamorpholino-s-triazolo[4,3-b]pyridazine;
50. 3-(1-methyl-2-nitro-5-imidazolyl)-6-methyl-s-triazolo-[4,3-b]pyridazine;
51. 3-(1-methyl-2-nitro-5-imidazolyl)-6-dimethylsulphimino-s-triazolo[4,3-b]pyridazine;
52. 3-(1-methyl-2-nitro-5-imidazolyl)-6-dimethylsulphoximino-s-triazolo[4,3-b]pyridazine;
53. 3-(1-methyl-2-nitro-5-imidazolyl)-s-triazolo[4,3-b]-pyridazine-6-carboximic acid ethyl ester;
54. 3-(1-methyl-2-nitro-5-imidazolyl)-s-triazolo[4,3-b]-pyridazine-6-carboxyhydrazidimide;
55. 1-methyl-2-[3-(1-methyl-2-nitro-5-imidazolyl)-6-(s-triazolo [4,3-b]pyridazinylimino)]pyrrolidine;
56. 3-(5-nitro-1-methyl-2-imidazolyl)-6-(1-piperazinyl-methyleneamino)-s-triazolo [4,3-b]pyridazine;
57. 3-(5-nitro-1-methyl-2-imidazolyl)-6-isopropylamino-s-triazolo [4,3-b]pyridazine.

Thus, the preferred compounds of general formula (I) are those which are substituted in the 1-position of the imidazolyl ring by a methyl radical; it is, however, to be understood that unsubstituted compounds, as well as compounds substituted by, for example, ethyl, n-propyl, isopropyl, butyl, 2-hydroxyethyl, 2-hydroxypropyl, 2-methoxyethyl, 2-acetoxyethyl, formyloxyethyl or similar groups also exhibit advantageous properties.

The following Examples are given for the purpose of illustrating, without limitation, the present invention:

EXAMPLE 1- PREPARATION OF
3-(5-NITRO-1-METHYL-2-IMIDAZOLYL)-6-MORPHOLINO-S-TRIAZOLO[4,3-b]PYRIDAZINE 0.7 crude 3-(5-nitro-1-methyl-2-imidazolyl)-6-chloro-s-triazolo[4,3-b]pyridazine was suspended in 5 ml. of a mixture of dioxan and methanol (1:1) and stirred for 1 hour at 60° C. with 1.3 g. morpholine, almost complete solution thereby temporarily occurring and subsequently the reaction product crystallized out. After cooling the reaction mixture and leaving it to stand for some time at ambient temperature, the product was filtered off with suction and washed with dioxan-methanol (1:1) and then with ether. There was obtained 0.66 g. of substance which, after recrystallization from 14 ml. dioxan, with the addition of active charcoal, gave 0.5 g. of the desired 3-(5-nitro-1-methyl-2-imidazolyl)-6-morpholino-s-triazolo-[4,3-b]pyridazine in the form of a yellow material which melts at 240° – 242° C.

EXAMPLE 2- PREPARATION OF
3-(5-NITRO-1-METHYL-2-IMIDAZOLYL)-6-DIMETHYLAMINO-S-TRIAZOLO[4,3-b]PYRIDAZINE 1.4 g. 3-(5-nitro-1-methyl-2-imidazolyl)-6-chloro-s-triazolo[4,3-b]pyridazine was suspended in 14 ml. of a mixture of dioxan and methanol (1:1), 6.7 ml. 30percent methanolic dimethylamine solution were added thereto, the reaction mixture was stirred for 1 hour at 60° C., then cooled in an ice bath, the product was filtered off with suction, washed with a mixture of dioxan and methanol (1:1) and then with ether and the product thus obtained (0.66 g.) recrystallized from 15 ml. dioxan-dimethylformamide (9:1), with the addition of charcoal, 0.35 g. of intense yellow crystals of the desired 3-(5-nitro-1-methyl-2-imidazolyl)-6-dimethylamino-s-triazolo[4,3-b]pyridazine thereby being obtained. It has a melting point of 233° –236° C.

EXAMPLE 3- PREPARATION OF
3-(5-NITRO-1-METHYL-2-IMIDAZOLYL)-6-(4-METHYLPIPERAZIN-1-YL-S-TRIAZOLO[4,3-b]PYRIDAZINE

In a manner analogous to that described in Example 1, from 1.4 g. 3-(5-nitro-1-methyl-2-imidazolyl)-6-chloro-s-triazolo[4,3-b]pyridazine and 3 g. 4-methylpiperazine, there was obtained 0.9 g. crude product which, after recrystallization from 25 ml. 80 percent aqueous isopropanol, with the addition of charcoal, and concentration of the mother liquor, gave 0.52 g. of yellowish-white 3-(5-nitro-1-methyl-2-imidazolyl)-6-(4-methylpiperazin-1-yl)-s-triazolo-[4,3-b]pyridazine, which has a melting point of 172° – 174° C.

EXAMPLE 4- PREPARATION OF 3-(5-NITRO-1-METHYL-2-IMIDAZOLYL)-6-PHTHALIMIDO-S-TRIAZOLO[4,3-b]PYRIDAZINE 3.5 g. 3-(5-nitro-1-methyl-2-imidazolyl)-6-chloro-s-triazolo[4,3-b]pyridazine were, together with 3.25 g. potassium phthalimide and 0.25 g. potassium iodide, finely powdered and then heated for 1.5 hours at 100° C. with 25 ml. dimethyl sulfoxide. After cooling the reaction mixture, it was mixed with 100 ml, ice water, the precipitated material was filtered off with suction after 30 minutes and washed with water. There was thus obtained 3.8 g. crude product which, after briefly boiling up with 38 ml. of a mixture of dimethyl formamide and water (2:1) and suction filtering while still hot, gave 1.9 g. 3-(5-nitro-1-methyl-2-imidazolyl)-6-phthalimido-s-triazolo[4,3-b]-pyridazine which melts, with decomposition, at 307° – 309° C.

EXAMPLE 5- PREPARATION OF 3-(5-NITRO-1-METHYL-2-IMIDAZOLYL)-6-AMINO-S-TRIAZOLO-[4,3-b]PYRIDAZINE 1.7 g. 3-(5-nitro-1-methyl-2-imidazolyl)-6-phthalimido-s-triazolo[4,3-b]pyridazine was heated for 1 hour with 17 ml. of a mixture of water and concentrated hydrochloric acid (2:3) at a bath temperature of 110° C. After leaving to cool overnight, the precipitated crystals were filtered off with suction, suspended in a little water, rendered alkaline with aqueous ammonia, again filtered off with suction and washed with water. There was thus obtained 0.74 g. of crude product which, after recrystallization from 9. ml. 80 percent aqueous dimethyl formamide, with the addition of charcoal, gave 0.6 g. of the desired 3-(5-nitro-1-methyl-2-imidazolyl)-6-amino-s-triazolo[4,3-b]pyridazine in the form of a yellow substance which melts, with foaming, at 275°–277° C.

EXAMPLE 6- PREPARATION OF N-[3-(5-NITRO-1-METHYL-2-IMIDAZOLYL)-S-TRIAZOLO[4,3-b]PYRIDAZIN-6-yl]-N',N'-DIMETHYLFORMAMIDINE 0.4 ml. dimethyl formamide was stirred with 2 ml. dioxan and 0.45 ml. phosphorous oxychloride for 1 hour at 30°–35° C and then mixed with 0.73 g. of the amine (crude product) obtained in EXAMPLE 5. 2 ml. dioxan were then added, the reaction mixture was further stirred for 1 hour at 30°–35° C., subsequently mixed with 30 ml. ice water, rendered alkaline with aqueous ammonia (pH 9–10), left to stand for 30 minutes and then filtered with suction and washed with water. There was thus obtained 0.6 g. of crude product. After recrystallization from 90% aqueous isopropanol, with the addition of charcoal, there was obtained 0.3 g. of the desired N-[3-(5-nitro-1-methyl-2-imidazolyl)-s-triazolo [4,3-b]pyridazin-6-yl]-N',N' -dimethylformamidine in the form of a yellow material which has a melting point of 246° – 247° C.

EXAMPLE 7- PREPARATION OF 3-(1-METHYL-5-NITRO-2-IMIDAZOLYL)-6-FORMYLAMINO-S-TRIAZOLO[4,3-b]PYRIDAZINE 100 mg. 3-(5-nitro-1-methyl-2-imidazolyl)-6-amino-s-triazolo[4,3-b]pyridazine were suspended in 1.3 ml. dimethyl formamide and, after the addition of 1.5 ml. of the mixed anhydride obtainable from formic acid and acetic anhydride, stirred at ambient temperature until no more starting material could be detected by thin layer chromatography. The almost clear solution thus obtained was, after filtration, evaporated in a vacuum and the residue brought to crystallization with ether. There were thus obtained 72 mg. (65 percent of theory) 3-(1-methyl-5-nitro-2-imidazolyl)-6-formylamino-s-triazolo[4,3-b]pyridazine in the form of yellowish crystals which melt, with decomposition, at 200° – 204° C.

EXAMPLE 8- PREPARATION OF 3-(5-NITRO-1-METHYL-2-IMIDAZOLYL)-6-METHYLAMINO-S-TRIAZOLO[4,3-b]PYRIDAZINE 1.96 g. 3-(5-nitro-1-methyl-2-imidazolyl)-6-chloro-s-triazolo[4,3-b]pyridazine was dissolved in 20 ml. hot dioxan, 2.7 ml. of a 35 percent aqueous methylamine solution were introduced at 60° C., while stirring, the reaction mixture was maintained for 1.5 hours at 60° C., cooled, left to stand for some time and the crystals obtained filtered off with suction, washed with dioxan and water and recrystallized (1.38 g.) from 20 ml. of a mixture of dioxan and dimethyl formamide (7:3), with the addition of charcoal. There was obtained 1.04 g. of the desired 3-(5-nitro-1-methyl-2-imidazolyl)-6-methylamino-s-triazolo[4,3-b]-pyridazine in the form of yellowish-white crystals which melt, with decomposition, at 260° – 262° C.

EXAMPLE 9- PREPARATION OF 3-(5-NITRO-1-METHYL-2-IMIDAZOLYL)-6-(1-PIPERIDINYL-METHYLENEAMINO-S-TRIAZOLO[4,3-b]PYRIDAZINE 2.85 ml. N-formyl-piperidine in 10 ml. dioxan were stirred with 2.4 ml. phosphorus oxychloride, which was introduced portionwise at 35° – 40° C., for 30 minutes at this temperature, then 1.5 g. crude 3-(5-nitro-1-methyl-2-imidazolyl)-6-amino-s-triazolo[4,3-b]pyridazine was added and the reaction mixture was stirred for 1.5 hours at 35° – 40° C. The solution obtained was now poured into 75 ml. ice water, filtered with suction and the clear filtrate was rendered alkaline (about pH 10) with concentrated aqueous ammonia, cooled, left to stand for some time and the resultant crystals (1.28 g.) filtered off with suction and recrystallized from 25 ml. isopropanol, with the addition of charcoal, 0.82 g. of the desired 3-(5-nitro-1-methyl-2-imidazolyl)-6-(1-piperidinyl-methyleneamino)-s-triazolo[4,3-b]pyridazine thereby being obtained in the form of yellowish-white crystals which melt at 187° – 189° C.

EXAMPLE 10- PREPARATION OF 3-(5-NITRO-1-METHYL-2-IMIDAZOLYL)-6-(MORPHOLINO-METHYLENEAMINO)-S-TRIAZOLO[4,3-b]PYRIDAZINE

In a manner analogous to that described in Example 9, from 1.35 ml. N-formyl-morpholine in 6 ml. dioxan, 1.2 ml. phosphorous oxychloride and 1.5 g. 3-(5-nitro-1-methyl-2-imidazolyl)-6-amino-s-triazolo[4,3- b]pyridazine, there was obtained, after a reaction period of 2 hours at 35° – 40° C. and pouring on to 75 ml. ice water, 0.76 g. of crude product which, after recrystallization from a mixture of 12 ml. isopropanol and dioxan (3:2), with the addition of charcoal, gave 0.4 g. of the desired 3-(5-nitro-1-methyl-2-imidazolyl)-6-(morpholino-methyleneamino)-s-triazolo[4,3-b]pyridazine in the form of yellow-white crystals which melt at 215° – 216° C. and change above 197° C.

EXAMPLE 11- PREPARATION OF 3-(5-NITRO-1-METHYL-2-IMIDAZOLYL)-6-ACETAMIDO-S-TRIAZOLO[4,3-b]PYRIDAZINE 1.45 g. 3-(5-nitro-1-methyl-2-imidazolyl)-6-amino-s-triazolo[4,3-b]pyridazine was boiled under reflux with 22 ml. acetic anhydride for 1.5 hours at 160° C. bath temperature, the solution obtained was then mixed with charcoal, suction filtered while still hot, washed with a little acetic anhydride and then with ether and dried for 3 hours at 120° C. There was thus obtained 0.79 g. of the desired 3-(5-nitro-1-methyl-2-imidazolyl)-6-acetamido-s-triazolo[4,3-b]pyridazine in the form of yellow-white crystals which melt at 238° – 239° C. and show a change above 230° C.

EXAMPLE 12- PREPARATION OF 3-(5-NITRO-1-METHYL-2-IMIDAZOLYL)-6-ETHYLAMINO-S-TRIAZOLO[4,3-b]PYRIDAZINE 1.12 g. 3-(5-nitro-1-methyl-2-imidazolyl)-6-chloro-s-triazolo[4,3-b]pyridazine was dissolved in 16 ml. boiling dioxan, a small amount of undissolved material was filtered off while the solution was still hot, the clear filtrate was mixed with 3.3 ml. 33 percent aqueous ethylamine solution, maintained for 2 hours at 60° C., the precipitated crystals were, after cooling and leaving to stand for some time, filtered off with suction, washed with dioxan and water and then dried in a vacuum at 120° C., 0.73 g. of the desired 3-(5-nitro-1-methyl-2-imidazolyl)-6-ethylamino-s-triazolo[4,3-b]pyridazine thereby being obtained. It has a melting point of 258° – 263° C.

EXAMPLE 13- PREPARATION OF 3-(5-NITRO-1-METHYL-2-IMIDAZOLYL)-6-(4-METHYLPIPERAZIN-1-YL-METHYLENEAMINO)-S-TRIAZOLO[4,3-b]PYRIDAZINE 1.15 g. 3-(5-nitro-1-methyl-2-imidazolyl)-6-amino-s-triazolo[4,3-b]pyridazine was stirred with 15 ml. ethyl orthoformate and 7.5 ml. acetic anhydride at a bath temperature of 130° C., then evaporated in a vacuum at 70° C. to give a residue of crude 3-(5-nitro-1-methyl-2-imidazolyl)-6-ethoxymethyleneamino-s-triazolo[4,3-b]pyridazine. A sample thereof, triturated with ethanol, melted at 134° – 135° C. The residue thus obtained was dissolved in 20 ml. of a mixture of isopropanol and dioxan (7:3) and 2.3 ml. 4-methylpiperazine added thereto at 20° C., while stirring. The crystals formed were filtered off with suction after about 15 minutes, washed with isopropanol and water and dried in a vacuum for 2 hours at 120° C. There was thus obtained 1.22 g. of the desired 3-(5-nitro-1-methyl-2-imidazolyl)-6-(4-methyl-piperazin-1-yl-methyleneamino)-s-triazolo[4,3-b]pyridazine which melts at 219° – 222° C.

EXAMPLE 14- PREPARATION OF 3-(5-NITRO-1-β-HYDROXYETHYL-2-IMIDAZOLYL)-6-DIMETHYLAMINO-S-TRIAZOLO[4,3-b]PYRIDAZINE 5 g. crude 3-(5-nitro-1-β-acetoxyethyl-2-imidazolyl)-6-chloro-s-triazolo[4,5-b]pyridazine were dissolved in 50 ml. of a mixture of dioxan and methanol (1:1), 5.4 ml. 40 percent aqueous dimethylamine were added thereto, the reaction mixture was stirred for 1 hour at 60° C., evaporated almost completely, the residue triturated with 20 ml. isopropanol, 1.6 g. of solid substance being obtained which has a melting point of 164° – 167° C. After recrystallization thereof from 55 ml. isopropanol, with the addition of charcoal, there was obtained 1 g. 3-(5-nitro-1-β-acetoxyethyl-2-imidazolyl)-6-dimethylamino-s-triazolo[4,3-b]-pyridazine in the form of green-yellow crystals with a melting point of 172° – 174° C. After hydrolysis of 0.4 g. of this substance with 8 ml. 2N hydrochloric acid (90 minutes at 50° C.), the desired compound can be obtained by evaporating the hydrochloric acid solution in a vacuum at 50° C., taking up the residue with 5 ml. water, adjusting to pH 8 – 9 with concentrated aqueous ammonia, filtering off with suction the crystals obtained, washing with water and drying for 2 hours at 120° C. There was thus obtained 0.32 g. 3-(5-nitro-1-β-hydroxyethyl-2-imidazolyl)-6-dimethylamino-s-triazolo[4,3-b]pyridazine, which has a melting point of 220° – 222° C.

The 3-(5-nitro-1-β-acetoxyethyl-2-imidazolyl)-6-chloro-s-triazolo[4,3-b]pyridazine used as starting material was prepared in the following manner:

5.4 g. crude, oily 5-nitro-1-β-acetoxyethyl-imidazolyl-2-aldehyde were dissolved in 54 ml. methanol and this solution introduced immediately into a solution, with a temperature of 40° C., of 3.8 g. 3-hydrazino-6-chloropyridazine in 50 ml. water and 3.6 ml. glacial acetic acid, maintained for 2 minutes at 40° C., then stirred for 1 hour at ambient temperature, suction filtered and washed with 50 percent aqueous methanol and finally with ether. There were thus obtained 4.5 g. 5-nitro-1-β-acetoxyethyl-imidazole-2-aldehyde-6-chloropyridazinyl-hydrazone, which has a melting point of 232° – 234° C. This substance was suspended in 67 ml. glacial acetic acid, 7.5 g. lead tetraacetate was added thereto portionwise, while stirring, the reaction mixture was further stirred for 30 minutes at 50° C., the clear solution was then evaporated, the residue was triturated with ice water, then shaken out with chloroform and the combined chloroform extracts evaporated to give 5 g. crude, oily 3-(5-nitro-1-β-acetoxyethyl-2-imidazolyl)-6-chloro-s-triazolo[4,3-b]pyridazine.

EXAMPLE 15- PREPARATION OF 3-(5-NITRO-1-METHYL-2-IMIDAZOLYL)-6-(AMINOMETHYLENE-AMINO)-S-TRIAZOLO[4,3-b]PYRIDAZINE

Crude 3-(5-nitro-1-methyl-2-imidazolyl)-6-ethoxymethyleneamino-s-triazolo[4,3-b]pyridazine, prepared according to Example 13, from 1.5 g. 3-(5-nitro-1-methyl-2-imidazolyl)-6-amino-s-triazolo[4,3-b]pyridazine, was dissolved in 20 ml. of a mixture of isopropanol and dioxan (7:3) and mixed, while stirring, with 2 ml. concentrated aqueous ammonia. Stirring was continued for 30 minutes at ambient temperature, solid material was then filtered off with suction, washed with isopropanol and water and the product obtained (1.27 g.) recrystallized from 10 ml. aqueous dimethyl formamide, with the addition of charcoal. After drying in a vacuum for 2 hours at 120° C., there was obtained 0.75 g. N-[3-(5-nitro-1-methyl-2-imidazolyl)-s-triazolo[4,3-b]pyridazin-6-yl]-formamidine which melts, with decomposition, at 200° – 202° C.

EXAMPLE 16- PREPARATION OF 3-(5-NITRO-1-METHYL-2-IMIDAZOLYL)-6-PROPIONAMIDO-S-TRIAZOLO[4,3-b]PYRIDAZINE

In a manner analogous to that described in Example 11, from 1.5 g. 3-(5-nitro-1-methyl-2-imidazolyl)-6-amino-s-triazolo[ 4,3-b]pyridazine, 22ml. propionic acid anhydride and 0.05 g. p-toluene-sulphonic acid (1.5 hours at 130° C. bath temperature), there was obtained 1 g. 3-(5-nitro-1-methyl-2-imidazolyl)-6-propionamido-s-triazolo[4,3-b]pyridazine, which has a melting point of 211° – 213° C.

EXAMPLE 17- PREPARATION OF 3-(5-NITRO-1-METHYL-2-IMIDAZOLYL)-6-(ACETAMIDOMETHYLENE-AMINO)-S-TRIAZOLO[4,3-b]PYRIDAZINE 1 g. 3-(5-nitro-1-methyl-2-imidazolyl)-6-(aminomethyleneamino)-s-triazolo[4,3-b]pyridazine (see Example 15 for the preparation thereof) was stirred for 2hours at 60° C. with 20 ml. acetic anhydride, the precipitated crystals thereafter filtered off with suction, washed with acetic anhydride and with ether and dried for 2 hours in a vacuum at 120° C. There was thus obtained 1 g. of the desired 3-(5-nitro-1-methyl-2-imidazolyl)-6-(acetamidomethyleneamino)-o-triazolo[4,3-b]pyridazine, which has a melting point of 237° – 241° C.

EXAMPLE 18- PREPARATION OF 3-(5-NITRO-1-METHYL-2-IMIDAZOLYL)-6-(DIETHYLAMINO-METHYLENEAMINO)-S-TRIAZOLO[4,3-b]PYRIDAZINE

In a manner analogous to that described in Example 13, from 1 g. 3-(5-nitro-1-methyl-2-imidazolyl)-6-amino-s-triazolo [4,3-b]pyridazine and 10 ml. ethyl orthoformate, there was prepared crude 3-(5-nitro-1-methyl-2-imidazolyl)-6-ethoxymethyleneamino-s-triazolo[4,3-b]pyridazine which, with 13 ml. of a solvent mixture of isopropanol and dioxan (7:3) and 1.1 ml. diethylamine gave, after a reaction time of 30 minutes at 20° C., subsequent evaporation of the solution in a vacuum at a bath temperature of 80° C., trituration of the residue with a little isopropanol and water and drying for 2 hours at 120° C. in a vacuum, 0.84 g. of the desired 3-(5-nitro-1-methyl-2-imidazolyl)-6-(diethylaminomethyleneamino)-s-triazolo[4,3-b]pyridazine which has a melting point of 155° – 156° C.

EXAMPLE 19- PREPARATION OF 3-(5-NITRO-1-METHYL-2-IMIDAZOLYL)-6-METHYLAMINO-METHYLENEAMINO)-S-TRIAZOLO[4,3-b]PYRIDAZINE

In a manner analogous to that described in Example 13, from 1 g. 3-(5-nitro-1-methyl-2-imidazolyl)-6-amino-s-triazolo[4,3-b]pyridazine and 10 ml. ethyl orthoformate, there was obtained crude 3-(5-nitro-1-methyl-2-imidazolyl)-6-ethoxymethyleneamino-s-triazolo[4,3-b]pyridazine which, after reaction with 1.4 ml. 35 percent aqueous methylamine for 30 minutes at 20° C., gave 1.03 g. of the desired 3-(5-nitro-1-methyl-2-imidazolyl)-6-(methylaminomethyleneamino)-s-triazolo[4,3-b]pyridazine, which has a melting point of 253° – 255° C.

EXAMPLE 20- PREPARATION OF 3-(5-NITRO-1-METHYL-2-IMIDAZOLYL)-6-PIPERIDINO-S-TRIAZOLO[4,3-b]PYRIDAZINE

In a manner analogous to that described in Example 12, from 1.4 g. 3-(5-nitro-1-methyl-2-imidazolyl)-6-chloro-s-triazolo[4,3-b]pyridazine and 2.55 ml. piperidine, there ws obtained 1.55 g. of the desired 3-(5-nitro-1methyl-2-imidazolyl)-6-piperidino-s-triazolo[4,3-b]pyridazine, which has a melting point of 215° – 217° C.

EXAMPLE 21- PREPARATION OF 3-(5-NITRO-1-β-ACETOXYETHYL-2-IMIDAZOLYL)-6-METHYLAMINO-S-TRIAZOLO[4,3-b]PYRIDAZINE 0.42 g. crude 3-(5-nitro-1-β-acetoxyethyl-2-imidazolyl)-6-chloro-s-triazolo[4,3-b]pyridazine (see Example 14 for the preparation thereof) was dissolved in 3 ml. dioxan, mixed with 0.36 ml. 33 percent aqueous methylamine solution, maintained at 60° C. for half an hour, then evaporated in a vacuum at a bath temperature of 50° C. The residue was dissolved in 2 ml. isopropanol, left to stand for about one hour at ambient temperature and the precipitated crystals then filtered off with suction, washed with isopropanol and ether and recrystallized (0.1 g.) from about 5 ml. isopropanol, with the addition of charcoal, to give 0.054 g. of the desired 3-(5-nitro-1-β-acetoxyethyl-2-imidazolyl)-6-methylamino-s-triazolo-[4,3-b]pyridazine, which has a melting point of 221° – 233° C.

EXAMPLE 22- PREPARATION OF 3-(5-NITRO-1-HYDROXYETHYL-2-IMIDAZOLYL)-6-METHYLAMINO-S-TRIAZOLO[4,3-b]PYRIDAZINE 1.2 g. of the crude acetyl compound obtained according to Example 21 was hydrolyzed with 24 ml. 2N hydrochloric acid for 1 hour at 50° C., the solution then evaporated, the residue dissolved in 4 ml. water, the pH adjusted, in the cold, to 8 to 9 with concentrated aqueous ammonia and left to stand for 1 hour. Solid material was then filtered off with suction and washed with water. There was thus obtained 0.88 g. of the desired 3-(5-nitro-1-β-hydroxyethyl-2-imidazolyl)-6-methylamino-s-triazolo[4,3-b]pyridazine which melts at 242° – 244° C. (contains about 0.5 mol water of crystallization per mol of compound).

EXAMPLE 23- PREPARATION OF 3-(5-NITRO-1-β-ACETOXYETHYL-2-IMIDAZOLYL)-6-(4-METHYL-1-PIPERAZINYL)-S-TRIAZOLO[4,3-b]PYRIDAZINE

In a manner analogous to that described in Example 21, 4.22 g. crude 3-(5-nitro-1-β-acetoxyethyl-2-imidazolyl)-6-chloro-s-triazolo[4,3-b]pyridazine were reacted with 4 g. 4-methylpiperazine in 20 ml. dioxan; after evaporation of the reaction mixture, the residue remaining behind was repeatedly digested with petroleum ether and then recrystallized from 15 ml. isopropanol, left to stand overnight and the crystals then filtered off with suction and washed with water. There were thus obtained 2.4 g. 3-(5-nitro-1-β-acetoxyethyl-2-imidazolyl)-6-(4-methyl-1-piperazinyl)-s-triazolo[4,3-b]pyridazine, which has a melting point of 168° – 170° C.

EXAMPLE 24- PREPARATION OF 3-(5-NITRO-1-β-HYDROXYETHYL-2-IMIDAZOLYL)-6-(4-METHYL-1-PIPERAZINYL)-S-TRIAZOLO[4,3-b]PYRIDAZINE 1.8 g. 3-(5-nitro-1-β-acetoxyethyl-2-imidazolyl)-6-(4-methyl-1-piperazinyl)-s-triazolo[4,3-b]pyridazine (obtained according to Example 23) was reacted for 1.5 hours at 50° C. with 36 ml. 2N hydrochloric acid. The solution was then treated with charcoal, evaporated in a vacuum and the residue dissolved in 10 ml. water, adjusted to about pH 9 with concentrated aqueous ammonia, left to stand for about 30 minutes and the precipitated crystals were filtered off with suction and washed with water and ether. There was thus obtained 1.1 g. of the desired 3-(5-nitro-1-β-hydroxyethyl-2-imidazolyl)-6-(4-methyl-1-piperazinyl)-s-triazolo[4,3-b]pyridazine. After drying for 1.5 days in a vacuum at 70° C., the product has a melting point of 98° – 100° C. (foams up).

EXAMPLE 25- PREPARATION OF 3-(5-NITRO-1-ETHYL-2-IMIDAZOLYL)-6-DIMETHYLAMINO-S-TRIAZOLO[4,3-b]PYRIDAZINE

From 1.5 g. crude 3-(5-nitro-1-ethyl-2-imidazolyl)-6-chloro-s-triazolo[4,3-b]pyridazine and 3.5 ml. 4 percent aqueous dimethylamine, there was obtained, after stirring for 1 hour at 60° C. in a mixture of 25 ml. of dioxan and methanol (1:1), evaporation of the solution in a vacuum, trituration of the residue with water and drying of the crystals obtained at 120° C. in a vacuum, 1.53 g. of the desired 3-(5-nitro-1-ethyl-2-imidazolyl)-6-dimethylamino-s-triazolo[4,3-b]pyridazine, which has a melting point of 191° – 193° C.

EXAMPLE 26- PREPARATION OF 3-(5-NITRO-1-ETHYL-2-IMIDAZOLYL)-6-CHLORO-S-TRIAZOLO-[4,3-b]PYRIDAZINE

From 20.15 g. 5-nitro-1-ethyl-imdazole-2-aldehyde and 18 g. 3-hydrazino-6-chloropyridazine in 400 ml. 50 percent aqueous methanol, to which 8 ml. glacial acetic acid had been added, there ws obtained, after 15 minutes at 60° C., 16.15 g. of the crude hydrazone which was introduced portionwise at 50° C. into a suspension of 35 g. lead tetraacetate in 318 ml. glacial acetric acid. The resultant solution was further stirred for 15 minutes at this temperature, then evaporated in a vacuum, the residue triturated with water, filtered off with suction and the dried product boiled out with 200 ml. dioxan and hot suction filtered from undissolved inorganic material. The filtrate was evaporated in a vacuum, the residue was triturated with water and undissolved organic material was filtered off with suction and dried to give 12.32 g. crude 3-(5-nitro-1-ethyl-2-imidazolyl)-6-chloro-s-triazolo[4,3-b]pyridazine, which has a melting point of 164° – 166° C.

EXAMPLE 27- PREPARATION OF 3-(5-NITRO-1-METHYL-2-IMIDAZOLYL)-6-DIMETHYLSULFIMINO-S-TRIAZOLO[4,3-b]PYRIDAZINE 0.52 g. 3-(5-nitro-1-methyl-2-imidazolyl)-6-amino-s-triazolo[4,3-b]pyridazine was dissolved in 7 ml. dimethyl sulfoxide, 2 ml. pyridine and 0.55 ml. triethylamine; at 50° C. and with stirring, 0.35 ml. methanesulfochloride, dissolved in 2 ml. dioxan, were added thereto dropwise, the reaction mixture then stirred for 1 hour at 50° C., the solution thereafter evaporated in a vacuum, the residue treated three times with ether, subsequently triturated with water, made very alkaline with concentrated aqueous ammonia, cooled for some time and the precipitated material then filtered off with suction, washed with water and dried for 2 hours at 120° C. in a vacuum. There was thus obtained 0.35 g. of the desired 3-(5-nitro-1-methyl-2-imidazolyl)-6-dimethylsulfimino-s-triazolo[4,3-b]pyridazine, which has a melting point of 224° – 225° C.

EXAMPLE 28- PREPARATION OF 3-(5-NITRO-1-METHYL-2-IMIDAZOLYL)-6-(β-HYDROXYETHYL-AMINOMETHYLENEAMINO)-S-TRIAZOLO[4,3-b]PYRIDAZINE 1.2 g. crude 3-(5-nitro-1-methyl-2-imidazolyl)-6-ethoxymethyleneamino-s-triazolo[4,3-b]pyridazine was dissolved in 13 ml. isopropanol-dioxan mixture (7:3), 1 ml. ethanolamine was added thereto at 20° C., while stirring, and stirring was then continued for 30 minutes. The precipitated crystals were filtered off with suction, washed with isopropanol and water and dried for 2 hours at 120° C. in a vacuum. There was obtained 1.07 g. of the desired 3-(5-nitro-1-methyl-2-imidazolyl)-6-(β-hydroxyethylaminomethyleneamino)-s-triazolo[4,3-b]pyridazine, which has a melting point of 191° – 192° C.

EXAMPLE 29- PREPARATION OF 3-(5-NITRO-1-METHYL-2-IMIDAZOLYL)-6-(S,S-DIMETHYLSULFOXIMINO)-S-TRIAZOLO[4,3-b]PYRIDAZINE 2 g. 3-(5-nitro-1-methyl-2-imidazolyl)-6-azido-s-triazolo[4,3-b]pyridazine were heated, while stirring, with 20 ml. dimethyl sulfoxide for 1 hour at a bath temperature of 200° C. and the solution then evaporated under oil pump vacuum at a bath temperature of 90° C. The residue was triturated with water, filtered off with suction and dried. There was thus obtained 1.96 g. of the desired compound in crude form. After boiling out with 30 ml. of a mixture of dioxan and toluene (3:1), filtering off insoluble material with suction, cooling the filtrate, separating the crystals which thereby precipitated out and drying them at 120° C. in a vacuum, there was obtained 0.67 g. of the desired 3-(5-nitro-1-methyl-2-imidazolyl)-6-(S,S-dimethylsulfoximino)-s-triazolo[4,3-b]pyridazine, which has a melting point of 218° – 219° C.

EXAMPLE 30- PREPARATION OF 3-(5-NITRO-1-METHYL-2-IMIDAZOLYL)-6-(N-METHYL-N-β-HYDROXYETHYLAMINOMETHYLENEAMINO)-S-TRIAZOLO[4,3-b]-PYRIDAZINE 1.2 g crude 3-(5-nitro-1-methyl-2-imidazolyl)-6-ethoxymethyleneamino-s-triazolo[4,3-b]pyridazine was dissolved in 13 ml. of a mixture of isopropanol and dioxan (7:3), 1.15 ml. β-methyleneaminoethanol added thereto at 20° C., with stirring, the crystals obtained filtered off with suction after stirring for 30 minutes, washed with isopropanol and water and dried for 2 hours at 120° C. in a vacuum. There was thus obtained 1 g. 3-(5-nitro-1-methyl-2-imidazolyl)-6-(N-methyl-N-β-hydroxyethylaminomethyleneamino)-s-triazolo[4,3-b]pyridazine, which has a melting point of 183° – 186° C.

EXAMPLE 31- PREPARATION OF 3-(5-NITRO-1-METHYL-2-IMIDAZOLYL)-6-(CYCLOHEXYLAMINO-METHYLENEAMINO)-S-TRIAZOLO[4,3-b]PYRIDAZINE 1.2 g. crude 3-(5-nitro-1-methyl-2-imidazolyl)-6-ethoxymethyleneamino-s-triazolo[4,3-b]pyridazine was dissolved in 13 ml. of a mixture of isopropanol and dioxan (7:3) and mixed at 20° C. with 1.5 ml. cyclohexylamine. After 30 minutes, the precipitated crystals were filtered off with suction, washed with isopropanol and water and dried for 2 hours at 120° C. in a vacuum. There was obtained 0.8 g. of the desired 3-(5-nitro-1-methyl-2-imidazolyl)-6-(cyclohexylaminomethyleneamino)-s-triazolo[4,3-b]pyridazine, which has a melting point of 198° – 200° C.

EXAMPLE 32- PREPARATION OF 3-(5-NITRO-1-METHYL-2-IMIDAZOLYL)-6-(4-HYDROXY-1-PIPERIDINYL-METHYLENEAMINO)-S-TRIAZOLO[4,3-b]PYRIDAZINE 1.2 g. crude 3-(5-nitro-1-methyl-2-imidazolyl)-6-ethoxymethyleneamino-s-triazolo[4,3b]pyridazine dissolved in 13 ml. of a mixture of isopropanol and dioxan (7:3), was mixed, while stirring at 20° C., with 4-hydroxypiperidine. After 30 minutes, the precipitated crystals were filtered off with suction, washed with isopropanol and water and dried at 120° C. in a vacuum. There was thus obtained 0.6 g. of the desired 3-(5-nitro-1-methyl-2-imidazolyl)-6-(4-hydroxy-1-piperidinyl-methyleneamino)-s-triazolo[4,3-b]-pyridazine, which has a melting point of 188° – 190° C.

In an analogous manner, from 3-(5-nitro-1-methyl-2-imidazolyl)-6-ethoxymethyleneamino-s-triazolo[4,3-b]-pyridazine and 4-methylpiperidine, there was obtained 3-(5-nitro-1-methyl-2-imidazolyl)-6-(4-methyl-piperidino-methyleneamino)-s-triazolo[4,3-b]pyridazine.

EXAMPLE 33- PREPARATION OF 1-METHYL-2-[3-(5-NITRO-1-METHYL-2-IMIDAZOLYL)-6-(S-TRIAZOLO[4,3-b]PYRIDAZINYL)-IMINOL-PYRROLIDINE 1.4 ml. phosphorus oxychloride was added at 30° – 35° C., while stirring, to 1.5 ml. N-methylpyrrolidone in 7 ml. dioxan, the reaction mixture further stirred from 1 hour, then 2 g. 3-(5-nitro-1-methyl-2-imidazolyl)-6-amino-s-triazolo[4,3b]pyridazine added thereto, the reaction mixture further stirred for 1.5 hours at 35° – 40° C., poured into 100 ml. ice water, a small amount of insoluble material filtered off with suction, the clear filtrate then made markedly alkaline with concentrated aqueous ammonia and the crystals which thereby precipitated out were filtered off with suction, washed with water and ethanol and, after drying in a vacuum at 100° C., there was obtained 1.72 g. of crude product which, after recrystallization from 25 ml. of a mixture of dioxan and isopropanol (7:3) with the addition of charcoal, gave 1 g. of the desired 1-methyl-2-[3-(5-nitro-1-methyl-2-imidazolyl)-6-(s-triazolo[4,3-b]pyridazinyl)-imino]pyrrolidine, which has a melting point of 228° – 231° C.

Example 34- PREPARATION OF N-[3-(5-NITRO-1-METHYL-2-IMIDAZOLYL)-S-TRIAZOLO-[4,3-b]PYRIDAZIN-6-yl]-N-DIETHYLACETAMIDINE 1.4 ml. phosphorus oxychloride were added, with stirring, at 35° – 40° C. to 2 ml. diethylacetamide in 7 ml. dioxan, the reaction mixture maintained for 2 hours at this temperature, 2 g. 3-(5-nitro-1-methyl-2-imidazolyl)-6-amino-s-triazolo [4,3-b]pyridazine then added thereto, the reaction mixture further stirred for 2 hours at 35° – 60° C., subsequently poured into 100 ml. ice water, a small amount of by-products filtered off with suction, the filtrate adjusted to about pH 10 with concentrated aqueous ammonia, the precipitated material filtered off with suction and the filtrate left to stand overnight at ambient temperature. The crystals which thereby precipitate out were filtered off with suction, washed with water and dried in a vacuum. There was thus obtained 0.26 g. N-[3-(5-nitro-1-methyl-2-imidazolyl)-s-triazolo[4,3-b]pyridazin-6-yl]-N-diethylacetamidine, which has a melting point of 203°–205° C.

EXAMPLE 35- PREPARATION OF 1-METHYL-2-[3-(5NITRO-1-METHYL-2-IMIDAZOLYL)-6-(S-TRIAZOLO[4,3-b]PYRIDAZINYL)-IMINO]PIPERIDINE 1.6 ml. phosphorus oxychloride was added, while stirring, at 35° – 40° C. to a mixture of 1.8 ml. N-methyl-2-piperidone in 7 ml. dioxan, the reaction mixture further stirred for 1 hour, then mixed with 2 g. 3-(5-nitro-1-methyl-2-imidazolyl)-6-amino-s-triazolo[4,3-b]pyridazine, further stirred for 1.5 hours at 35° – 40° C., then poured into 100 ml. ice water, a small amount of insoluble material filtered off with suction, the filtrate adjusted to about pH 10 with concentrated aqueous ammonia, the precipitated crystals filtered off with suction, washed with water, dissolved in dilute aqueous hydrochloric acid, again separated off from a small amount of insoluble starting material and again rendered alkaline with concentrated aqueous ammonia. After cooling, the resultant crystals were filtered off with suction, washed with water, dried and recrystallized (1.05 g.) from 13 ml. dioxan, with the addition of charcoal, to give 0.83 g. of the desired 1-methyl-2-[3-(5-nitro-1-methyl-2-imidazolyl)-6-(s-triazolo[4,3-b]pyridazinyl)-imino]-piperidine; melting point 231°–232° C.

EXAMPLE 36- PREPARATION OF 3-(5-NITRO-1-METHYL-2-IMIDAZOLYL)-S-TRIAZOLO[4,3-b]-PYRIDAZINE.

4 g. lead tetraacetate were suspended in 40 ml. glacial acetic acid, 1.5 g. of the hydrazone obtained from 1.55 g. 5-nitro-1-methyl-imidazole-2-aldehyde and 1.1 g. 3-hydrazinopyridazine hydrochloride (prepared by heating for 30 minutes in 20 ml. 50 percent aqueous methanol at 50° C. and subsequent neutralization with sodium acetate) were added, while stirring at 50° – 60° C., the reaction mixture further stirred for 15 minutes, considerably evaporated in a vacuum, the resultant crystals filtered off with suction, triturated with water and dried for 2 hours in a vacuum at 120° C., 1.05 g. of the desired 3-(5-nitro-1-methyl-2-imidazolyl)-s-triazolo[4,3-b]pyridazine being obtained, which has a melting point of 235° – 237° C.

In an analogous manner, from 10 g. 5-nitro-1-methyl-imidazole-2-aldehyde and 10.2 g. 3-hydrazino-6-chloropyridazine, there were obtained 9.7 g. 3-(5-nitro-1-methyl-2-imidazolyl)-6-chloro-s-triazolo[4,3-b]pyridazine which after recrystallization from dioxan, with the addition of charcoal, has a melting point of 213°–214° C.

EXAMPLE 37-PREPARATION OF 3-(5-NITRO-1-METHYL-2-IMIDAZOLYL)-6-METHOXY-S-TRIAZOLO[4,3-b]-PYRIDAZINE 1.96 g. crude 3-(5-nitro-1-methyl-2-imidazolyl)-6-chloro-s-triazolo[4,3-b]pyridazine was dissolved in 35 ml. of a mixture of dioxan and methanol (1:1), 0.84 g. sodium methylate added thereto, the reaction mixture heated under reflux for 1 hour, the solution then evaporated in a vacuum, the residue triturated with water, filtered with suction and dried at 120° C. in a vacuum. There was thus obtained 0.64 g. of the desired 3-(5-nitro-1-methyl-2-imidazolyl)-6-methoxy-s-triazolo[4,3-b]pyridazine, which has a melting point of 193° – 198° C.

EXAMPLE 38- PREPARATION OF 3-(5-NITRO-1-METHYL-2-IMIDAZOLYL)-6-AZIDO-S-TRIAZOLO[4,3-b]PYRIDAZINE 0.56 g. 3-(5-nitro-1-methyl-2-imidazolyl)-6-chloro-s-triazolo[4,3-b]pyridazine was dissolved in 12 ml. 90 percent aqueous dimethyl sulfoxide at an elevated temperature, 0.46 g. sodium azide added thereto and then 1 ml. 2N hydrochloric acid, whereafter the reaction mixture was stirred for about 60 minutes at about 95° C., a clear solution being formed after about 3 minutes from which, after a further 5 minutes, crystallization commenced. The reaction mixture was then allowed to cool and, after standing for 1 hour, the crystals were filtered off with suction, washed with water, ethanol and ether and, after drying in a vacuum at about 110° C., there was obtained 0.5 g. of crude crystals (m.p. 208°–212° C. with foaming up). After recrystallization from 11 ml. dioxan, there was obtained 0.35 g. of the desired 3-(5-nitro-1-methyl-2-imidazolyl)-6azido-s-triazolo[4,3-b]pyridazine which melts, with foaming up at 208°–210° C.

In an analogous manner, from 2.1 g. 3-(5-nitro-1-methyl-2-imidazolyl)-6-chloro-s-triazolo[4,3-b]pyridazine and 1.13 g. sodium methane-sulfinate, there were obtained 1.8 g. 3-(5-nitro-1-methyl-2-imidazolyl)-6-methyl-sulfonyl-s-triazolo[4,3-b]pyridazine, which has a melting point of 202° – 204° C.

EXAMPLE 39- PREPARATION OF 3-(5-NITRO-1-METHYL-2-IMIDAZOLYL)-6-CYANO-S-TRIAZOLO[4,3-b]PYRIDAZINE 15.8 g. of the hydrazone prepared from 5-nitro-1-methyl-imidazole-2-aldehyde and 3-hydrazino-6-cyano-pyridazine (m.p. 246°–252° C) were suspended in 290 ml. glacial acetic acid, 33.5 g. lead tetraacetate were then added portionwise at 50° C for 30 minutes. The solution was then evaporated in a vacuum at a bath temperature of 50° C., the residue was triturated with ice water, filtered off with suction and, after drying, there were thus obtained 12.8 g. of crude product (m.p. 182° – 190° C.) which was dissolved in 320 ml. hot ethylene chloride and treated with charcoal. The clear filtrate was concentrated in a vacuum to a volume of about 30 ml. There were thus obtained 7 g. of the desired 3-(5-nitro-1-methyl-2-imidazolyl)-6-cyano-s-triazolo [4,3-b]pyridazine, which has a melting point of 212° – 216° C.

The hydrazone used as starting material was prepared in the following manner:

10.9 g. 5-nitro-1-methyl-imidazole-2-aldehyde were suspended in 156 ml. water, 47 ml. 2N hydrochloric acid were added thereto and the mixture heated to 50° C. A small amount of insoluble material was removed, to the clear filtrate was added, in a thin stream, a solution of 12.5 g. 3-hydrazino-6-cyanopyridazine in 203 ml. methanol and the reaction mixture was stirred for 5 minutes at 50° C. After cooling and leaving to stand for 30 minutes at ambient temperature, the suspension was brought to pH 6 to 7 with methanolic ammonia, filtered off with suction and the crystals so obtained were washed with 50 percent aqueous methanol and ether. There were thus obtained 15.8 g. of the desired hydrazone.

EXAMPLE 40- PREPARATION OF 3-(5-NITRO-1-METHYL-2-IMIDAZOLYL)-6-CARBETHOXY-S-TRIAZOLO[4,3-b]PYRIDAZINE 7.5 g. 3-(5-nitro-1-methyl-2-imidazolyl)-6-cyano-s-triazolo[4,3-b]pyridazine were boiled with 225 ml. 17 percent ethanolic hydrochloric acid for 3 hours under reflux, left to stand overnight at ambient temperature, the small amount of crystals formed was filtered off with suction and the clear filtrate was evaporated in a vacuum. The evaporation residue was triturated with an aqueous solution of sodium carbonate and, after suction filtration, there were obtained 7.08 g. of crude crystals. 0.8 g. thereof was recrystallized, with the addition of charcoal, from 8 ml. of a mixture of dioxan and ethanol (6:4) to give 0.42 g. of the desired 3-(5-nitro-1-methyl-2-imidazolyl)-6-carbethoxy-s-triazolo[4,3-b]pyridazine, which has a melting point of 180° – 182° C.

EXAMPLE 41- PREPARATION OF 3-(5-NITRO-1-ETHYL-2-IMIDAZOLYL)-6-HYDRAZINO-S-TRIAZOLO[4,3-b]PYRIDAZINE 3 g. 3-(5-nitro-1-ethyl-2-imidazolyl)-6-chloro-s-triazolo[4,3-b] pyridazine were dissolved in 30 ml. of a mixture of dioxan and methanol (1:1) and 3 ml. hydrazine hydrate were added thereto at 20° – 25° C., while stirring. The reaction mixture was further stirred for 45 minutes and the separated crystals were filtered off with suction, washed with a mixture of dioxan and methanol (1:1) and dried in vacuum at 120° C. There was thus obtained 0.66 g. of the desired 3-(5-nitro-1-ethyl-2-imidazolyl)-6-hydrazino-s-triazolo[4,3-b]pyridazine which melts, with foaming up, at 216° – 223° C.

EXAMPLE 42- PREPARATION OF 3-(5-NITRO-1-METHYL-2-IMIDAZOLYL)-6-CARBOXY-S-TRIAZOLO[4,3-b]PYRIDAZINE 5.8 g. 3-(5-nitro-1-methyl-2-imidazolyl)-6-carbethoxy-s-triazolo[4,3-b]pyridazine were heated under reflux with 18.3 ml. 90 percent aqueous formic acid and 2.75 ml. methane-sulfonic acid for 3 hours at a bath temperature of 130° C. 80 ml. water were then added thereto and the precipitated crystals were filtered off with suction, after having stood for 1 hour, and washed with water. There were thus obtained 4.85 g. 3-(5-nitro-1-methyl-2-imidazolyl)-6-carboxy-s-triazolo[4,3-b]pyridazine, which has a melting point of 257° – 260° C. 1 g. of the product was recrystallized from 15 ml. dioxan with the addition of charcoal, to give 0.6 g. of pure product which melts, with foaming up, at 260° – 262° C.

EXAMPLE 43- PREPARATION OF 3-(5-NITRO-1-METHYL-2-IMIDAZOLYL)-6-CARBAMOYL-S-TRIAZOLO[4,3-b]PYRIDAZINE 1.54 g. crude 3-(5-nitro-1-methyl-2-imidazolyl)-6-carboxy-s-triazolo[4,3-b]pyridazine (m.p. 257° – 260° C.) was boiled under reflux for 1 hour with 16 ml. thionyl chloride. The solution was then evaporated to dryness and the residue triturated with trichloroethylene. Insoluble material was filtered off with suction and the crude acid chloride so obtained was immediately triturated with 10 ml. concentrated aqueous ammonia, then stirred for 1.5 hours at ambient temperature and, after suction filtration and washing with water, there was obtained 1 g. of the desired 3-(5-nitro-1-methyl-2-imidazolyl)-6-carbamoyl-s-triazolo[4,3-b]pyridazine. After recrystallization from 15 ml. 80% aqueous dimethyl formamide, with the addition of charcoal, the product melts, with foaming up, at 272° – 275° C. The yield is 0.7 g.

In an analogous manner, from 1 g. 3-(5-nitro-1-methyl-2-imidazolyl)-6-carboxy-s-triazolo[4,3-b]pyridazine, thionyl chloride and 10.5 ml. 3 percent aqueous methylamine, there was obtained 0.48 g. 3-(5-nitro-1-methyl-2-imidazolyl)-6-(N-methylcarbamoyl)-s-triazolo[4,3-b]pyridazine which melts, with foaming up, at 268° – 270° C.

EXAMPLE 44- PREPARATION OF 3-(5-NITRO-1-METHYL-2-IMIDAZOLYL)-6-(N-n-BUTYLCARBAMOYL)-s-TRIAZOLO[4,3-b]PYRIDAZINE

Proceeding in a manner analogous to that described in EXAMPLE 43, from 1.4 g. crude 3-(5-nitro-1-methyl-2-imidazolyl)-s-triazolo[4,3-b]pyridazine-6-carboxylic acid chloride and 16.4 ml. 6 percent aqueous n-butylamine solution, there was obtained, after thoroughly stirring for 1 hour at ambient temperature, 0.5 g. 3-(5-nitro-1-methyl-2-imidazolyl)-6-(N-n-butylcarbamoyl)-s-triazolo[4,3-b]pyridazine, which has a melting point of 136° – 138° C.

EXAMPLE 45- PREPARATION OF 3-(1-METHYL-2-NITRO-5-IMIDAZOLYL)-6-MORPHOLINO-S-TRIAZOLO[4,3-b]PYRIDAZINE

METHOD I:

2.8 g. lead tetraacetate were added at ambient temperature to a solution of 1.4 g. 1-methyl-2-nitroimidazole-5-carbaldehyde-(6-morpholino-3-pyridazinyl)-hydrazone in 9 ml. trifluoroacetic acid and 9 ml. glacial acetic acid, the internal temperature thereby increasing to 38° C. Subsequently, the reaction mixture was stirred for 30 minutes at 55°–60° C. and then evaporated in a vacuum. From the black-brown residue, a yellow product crystallized out which was washed with ice water. There was thus obtained 0.7 g. (50 percent of theory) of the desired 3-(1-methyl-2-nitro-5-imidazolyl)-6-morpholino-s-triazolo[4,3-b]pyridazine.

The 1-methyl-2-nitroimidazole-5-carbaldehyde-(6-morpholino-3-pyridazinyl)-hydrazone used as starting material was prepared in the following manner.

5.5 g. 1,5-dimethyl-2-nitroimidazole (see J. Med. Chem., 12, 779/1969) were dissolved in 61 ml. glacial acetic acid and 60.5 ml. acetic anhydride, 9.1 ml. concentrated sulfuric acid were added thereto, while stirring and cooling with ice, and subsequently 10.7 g. chromium trioxide were added thereto portionwise, a slight warming up being observed. After 30 minutes at 30° C., the reaction mixture was poured on to ice, neutralized and extracted with chloroform. The extract was washed with water, dried and evaporated. There was thus obtained 7.8 g. (78 percent of theory) of an oil which gradually crystallized. According to the molecular weight determined by mass spectrometry, this compound is the diacetate of 1-methyl-2-nitro-imidazole-5-carbaldehyde, 2.8 g. of this compound were stirred for 30 minutes under reflux in 28 ml. methanol and 2.8 ml. concentrated hydrochloric acid with 1.95 g. 3-hydrazino-6-morpholino-pyridazine (see Chem. Abstracts, 68, 59598 h/1968). The reaction mixture was then neutralized with sodium acetate, an orange-yellow suspension being formed. This was filtered off with suction and washed with water and methanol. There was obtained 0.95 g. (29 percent of theory) 1-methyl-2-nitro-imidazole-5-carbaldehyde-(6-morpholino-3-pyridazinyl)-hydrazone, which melts, with decomposition, at 268° – 271° C.

METHOD II:

1 g. 3-(1-methyl-2-nitro-5-imidazolyl)-6-chloro-s-triazolo[4,3-b]pyridazine was suspended in 10 ml. morpholine and stirred for 1 hour at ambient temperature. Then, after ascertaining completion of the reaction by thin layer chromatography, the reaction mixture was mixed with 40 ml. water, filtered with suction and washed with water and with methanol. There was thus obtained 1 g. (85 percent of theory) of the desired 3-(1-methyl-2-nitro-5-imidazolyl)-6-morpholino-s-triazolo[4,3-b]pyridazine, which has a melting point of 242° – 244° C. and showed no melting point depression in admixture with the compound prepared according to Method I above.

METHOD III:

0.55 g. 3-(1-methyl-2-amino-5-imidazolyl)-6-morpholino-s-triazolo[4,3-b]pyridazine were diazotized in tetrafluoroboric acid and reacted with sodium nitrite in the presence of copper powder (method analogous to the preparation of 1,5-dimethyl-2-nitroimidazole from the corresponding amino compound as described in J. Med. Chem. 12, 779/1969). The desired compound was obtained in the form of yellow crystals, the identity of which with the compound prepared according to Method I above is ascertained by thin layer chromatography and mass spectrum.

In an analogous manner, from 1.6 g 3-(1-methyl-2-amino-5-imidazolyl)-s-triazolo[4,3-b]pyridazine hydrochloride, there was obtained 0.5 g. 3-(1-methyl-2-nitro-5-imidazolyl)-s-triazolo [4,3-b]pyridazine, which was purified by column chromatography. The product was obtained in the form of orange-yellow crystals which melt with decomposition, at 222° – 225° C.

EXAMPLE 46- PREPARATION OF 3-(1-METHYL-2-NITRO-5-IMIDAZOLYL)-6-CHLORO-S-TRIAZOLO[4,3-b]PYRIDAZINE 0.8 g. of the diacetate of 1-methyl-2-nitroimidazole-5-carbaldehyde were stirred under reflux in 6.5 ml. methanol and 0.65 ml. concentrated hydrochloric acid with 0.4 g. 3-hydrazino-6-chloro-pyridazine. After 5 minutes, the reaction mixture was cooled, suction filtered, neutralized with an aqueous solution of sodium bicarbonate and washed with water and methanol. There was thus obtained 0.5 g. (64 percent of theory) 1-methyl-2-nitrimidazole-5-carbaldehyde-(6-chloro-3-pyridazinyl)-hydrazone. 3.5 g. of this hydrazone were reacted in 56 ml. glacial acetic acid with 7.2 g. lead tetraacetate to give 1.65 g. (47 percent of theory) 3-(1-methyl-2-nitro-5-imidazolyl)-6-chloro-s-triazolo[4,3-b]pyridazine, which has a melting point of 192°–195° C. The molecular weight was confirmed by the mass spectrum.

EXAMPLE 47- PREPARATION OF 3-(1-METHYL-2-NITRO-5-IMIDAZOLYL)-6-DIMETHYLAMINO-S-TRIAZOLO[4,3-b]PYRIDAZINE 0.5 g. 3-(1-methyl-2-nitro-5-imidazolyl)-6-chloro-s-triazolo[4,3-b]pyridazine were dissolved, with heating, in 10 ml. dimethyl formamide and gaseous dimethylamine passed in at 60° C. over the course of 15 minutes. The resultant suspension was then diluted with 6 ml. water, filtered with suction, first washed with aqueous dimethyl formamide, then with water and finally with methanol. There was thus obtained 0.4 g. (78 percent of theory) of the desired 3-(1-methyl-2-nitro-5-imidazolyl)-6-dimethylamino-s-triazolo[4,3-b]pyridazine in the form of yellow crystals which melt, with decomposition, at 261° – 263° C.

EXAMPLE 48- PREPARATION OF 3-(1-METHYL-2-NITRO-5-IMIDAZOLYL)-6-[N-METHYL-N-(β-DIMETHYLAMINOETHYL)-AMINO]-S-TRIAZOLO[4,3-b]PYRIDAZINE 0.65 g. 3-(1-methyl-2-nitro-5-imidazolyl)-6-chloro-s-triazolo[4,3-b]pyridazine were reacted in 13 ml. dimethyl formamide with 0.5 g. trimethylethylenediamine at 60° C. for 15 minutes. After working up the reaction mixture in a manner analogous to that described in Example 47, there was obtained 0.6 g. (75 percent of theory) of the desired 3-(1-methyl-2-nitro-5-imidazolyl)-6-[N-methyl-N-(β-dimethyl-aminoethyl)-amino]-s-triazolo[4,3-b]pyridazine in the form of yellow crystals which have a melting point of 196° – 198° C.

EXAMPLE 49- PREPARATION OF 3-(1-METHYL-2-NITRO-5-IMIDAZOLYL)-6-AMINO-S-TRIAZOLO[4,3-b]PYRIDAZINE 1.3 g. 3-(1-methyl-2-nitro-5-imidazolyl)-6-chloro-s-triazolo[4,3-b]pyridazine was dissolved in 10 ml. dimethyl sulfoxide, 0.7 g. of the sodium salt of methanesulfinic acid were added thereto and the reaction mixture was stirred for 1.5 hours at ambient temperature. The suspension was then diluted with water, filtered with suction and washed with water, methanol and finally with ether. There was thus obtained 1.4 g. (93 percent of theory) 3-(1-methyl-2-nitro-5-imidazolyl)-6-mesyl-s-triazolo[4,3-b]pyridazine which melts, with decomposition, at 245° – 249° C. 4.9 g. of this compound were dissolved in 120 ml. dimethyl sulfoxide and gaseous ammonia passed in over the course of 45 minutes at ambient temperature. The resultant suspension was filtered with suction and the yellow crystals obtained washed with water, methanol and finally with ether. There were thus obtained 3.8 g. (97 percent of theory) of the desired 3-(1-methyl-2-nitro-5-imidazolyl)-6-amino-s-triazolo[4,3-b]pyridazine which, upon heating, begins to sinter at 315° C. and slowly decomposes at 325° C.

EXAMPLE 50- PREPARATION OF 3-(1-METHYL-2-NITRO-5-IMIDAZOLYL)-6-DIMETHYLAMINO-METHYLENEAMINO)-S-TRIAZOLO[4,3-b]PYRIDAZINE 0.3 g. 3-(1-methyl-2-nitro-5-imidazolyl)-6-amino-s-triazolo[4,3-b]pyridazine were heated to 100° C., with stirring, for 2 hours in a mixture of 0.5 ml. dimethyl formamide-diethyl acetal and 0.3 ml. dimethyl formamide. The suspension was then cooled, diluted with alcohol, filtered off with suction and washed with alcohol. There was thus obtained 0.3 g. (83 percent of theory) of the desired 3-(1-methyl-2-nitro-5-imidazolyl)-6-(dimethylamino-methyleneamino)-s-triazolo[4,3-b]pyridazine in the form of yellow crystals which have a melting point of 233° – 235° C.

EXAMPLE 51- PREPARATION OF 3-(1-METHYL-2-NITRO-5-IMIDAZOLYL)-6-FORMYLAMINO-S-TRIAZOLO[4,3-b]PYRIDAZINE 1 g. 3-(1-methyl-2-nitro-5-imidazolyl)-6-amino-s-triazolo[4,3-b]pyridazine was suspended in 20 ml. acetic acidformic acid anhydride and stirred at a bath temperature of 80° C. After 4 hours, the reaction mixture was cooled, filtered with suction and the yellow crystals obtained were washed with methanol. After recrystallization from alcohol-dioxan, there was obtained 0.55 g. (50 percent of theory) of the desired 3-(1-methyl-2-nitro-5-imidazolyl)-6-formylamino-s-triazolo[4,3-b]pyridazine which melts at 224° – 226° C., with the evolution of gas.

EXAMPLE 52- PREPARATION OF 3-(1-METHYL-2-NITRO-5-IMIDAZOLYL)-6-(4-METHYL-1-PIPERAZINYL-METHYLENEAMINO)-S-TRIAZOLO[4,3-b]PYRIDAZINE 0.4 g. 3-(1-methyl-2-nitro-5-imidazolyl)-6-(ethoxymethyleneamino)-s-triazolo[4,3-b]pyridazine (obtained from the amino compound described in Example 49 by heating with triethyl orthoformate in the presence of acetic anhydride) was dissolved in a mixture of 3 ml. dioxan, 7 ml. isopropanol and 3 ml. dimethyl formamide, mixed at 40° C. with 0.2 g. N-methyl-piperazine and thereafter stirred for 30 minutes. Crystallization took place after a short time. The yellow crystals obtained were filtered off with suction and washed with ether. There was thus obtained 0.25 g. (53 percent of theory) of the desired 3-(1-methyl-2-nitro-5-imidazolyl)-6-(4-methyl-1-piperazinyl-methyleneamino)-s-triazolo[4,3-b]pyridazine, which has a melting point of 233° – 235° C.

EXAMPLE 53- PREPARATION OF 3-(1-METHYL-2-NITRO-5-IMIDAZOLYL)-6-(PIPERIDINO-METHYLENEAMINO)-S-TRIAZOLO[4,3-b]PYRIDAZINE.

1.1 g. 3-(1-methyl-2-nitro-5-imidazolyl)-6-amino-s-triazolo[4,3-b]pyridazine was suspended in 1.1 ml. dimethyl formamide, mixed with 2 g. dimethoxymethylpiperidine and stirred for 1.5 hours at 100° C. The reaction mixture was then cooled, mixed with methanol and filtered off with suction. After recrystallization from methanol with the addition of a little dimethyl formamide, there was obtained 0.75 g. (50 percent of theory) of the desired 3-(1-methyl-2-nitro-5-imidazolyl)-6-(piperidino-methyleneamino)-s-triazolo[4,3-b]pyridazine in the form of yellow crystals which melt at 205° – 208° C.

EXAMPLE 54- PREPARATION OF 3-(5-NITRO-1-ETHYL-2-IMIDAZOLYL)-6-(DIMETHYLAMINO-METHYLENEAMINO)-S-TRIAZOLO[4,3-b]PYRIDAZINE 1.6 ml. phosphorus oxychloride was added at 30° – 35° C. with stirring, to a mixture of 1.4 ml. dimethyl formamide in 7 ml. dioxan, the reaction mixture further stirred for 1 hour, 2 g. crude 3-(5-nitro-1-ethyl-2-imidazolyl)-6-amino-s-triazolo[4,3-b]pyridazine added thereto, the reaction mixture further stirred for 1.5 hours at 35° – 40° C., then poured into 100 ml. icewater, a small amount of insoluble material filtered off with suction, the filtrate rendered alkaline with concentrated aqueous ammonia, while cooling with ice, then left to stand for some time, whereafter the crystals formed were filtered off with suction, washed with water, dried in a vacuum at 120° C. and recrystallized (1.8 g.) from 50 ml. isopropanol, with the addition of charcoal. There was obtained 1.2 g. of the desired 3-(5-nitro-1-ethyl-2-imidazolyl)-6-(dimethylaminomethyleneamino)-s-triazolo[4,3-b]pyridazine, which melts at 198° – 200° C., a change occurring at 193° C.

EXAMPLE 55- PREPARATION OF 3-(5-NITRO-1-ETHYL-2-IMIDAZOLYL)-6-AMINO-S-TRIAZOLO[4,3-b]PYRIDAZINE 5 g. 3-(5-nitro-1-ethyl-2-imidazolyl)-6-chloro-s-triazolo[4,3-b]pyridazine, suspended in 33 ml. dimethyl sulfoxide, are mixed with 2.6 g. of the sodium salt of methanesulfinic acid, stirred for 1.5 hours at 20° C., gaseous ammonia passed in for 30 minutes, while stirring, at 50° C., cooled, diluted with 65 ml. water, the precipitated material filtered off with suction, washed with water and dried. There were obtained 4.14 g. crude 3-(5-nitro-1-ethyl-2-imidazolyl)-6-amino-s-triazolo[4,3-b]pyridazine, which has a melting point of 218° – 222° C.

EXAMPLE 56- PREPARATION OF 3-(5-NITRO-1-METHYL-2-IMIDAZOLYL)-6-(DI-N-PROPYLAMINO-METHYLENEAMINO)-S-TRIAZOLO[4,3-b]PYRIDAZINE 1.2 g. crude 3-(5-nitro-1-methyl-2-imidazolyl)-6-ethoxy-methyleneamino-s-triazolo[4,3-b]pyridazine, dissolved in 13 ml. of a mixture of isopropanol and dioxan (7:3), was mixed, while stirring, at 20° C. with 1.6 ml. di-n-propylamine, further stirred for 30 minutes, then evaporated in a vacuum and the oily residue triturated with isopropanol and water (1:1). Insoluble material was filtered off with suction and recrystallized from 12 ml. isopropanol and water (1:1), with the addition of charcoal. After drying at 100° C. in a vacuum, there was obtained 0.7 g. of the desired 3-(5-nitro-1-methyl-2-imidazolyl)-6-(di-n-propylaminomethyleneamino) 4,3-b]pyridazine, which has a melting point of 155° – 157° C.

EXAMPLE 57- PREPARATION OF 3-(5-NITRO-1-METHYL-2-IMIDAZOLYL)-6-ETHOXYMETHYLENEAMINO-S-TRIAZOLO[4,3-b]PYRIDAZINE.

1.15 g. 3-(5-nitro-1-methyl-2-imidazolyl)-6-amino-s-triazolo[4,3-b]pyridazine was stirred with 15 ml. ethyl orthoformate and 7.5 ml. acetic anhydride at a bath temperature of 130° C., then evaporated in a vacuum at 70° C., the residue obtained being crude 3-(5-nitro-1-methyl-2-imidazolyl)-6 -ethoxymethyleneamino-s-triazolo[4,3-b]pyridazine. A sample thereof, after trituration with ethanol, has a melting point of 134° – 135° C.

As noted above, the new nitroimidazolyl-triazolopyridazine compounds possess outstanding in vitro and in vivo antimicrobial action, particularly against Protozoa, such as Trichomonades and Salmonellae, which may be present in the digestive or other systems of mammals. This utility is, of course, snared by the pharmacologically acceptable salts of the pyridazine compounds, which salts are conventional in the art.

The pharmacologically compatible salts of the compounds of general formula (I) can be prepared, for example, by neutralization of the basic amino group thereof with non-toxic inorganic or organic acids. Examples of acids which can be used for this purpose include hydrochloric acid, sulfuric acid, phosphoric acid, hydrobromic acid, acetic acid, lactic acid, citric acid, oxalic acid, malic acid, salicylic acid, malonic acid, maleic acid, succinic acid and alkyl-sulfonic acids. In the case of compounds in which A is a carboxyl radical, corresponding salts can be obtained by reaction with appropriate inorganic or organic bases. As physiologically compatible salts, there may be mentioned, by way of example, the alkali metal, alkaline earth metal and ammonium salts, which can be prepared, for example by reaction with an aqueous solution of sodium hydroxide, potassium hydroxide or ammonia or of a corresponding carbonate.

The compounds of general formula (I) can be administered orally or parenterally, in admixture with a solid or liquid pharmaceutical diluent or carrier. As injection medium, it is preferred to use water which contains the stabilizing agents, solubilizing agents and/or buffers conventional for injection solutions. Additives of this type include, for example, tartrate or borate buffers, ethanol, dimethyl sulphoxide, complex-forming agents, (such as ethylenediamine-tetraacetic acid), high molecular weight polymers (such as liquid polyethylene oxide) for viscosity regulation or polyoxyethylene derivatives of sorbitan anhydrides.

Solid carrier materials include, for example, starch, lactose, mannitol, methyl cellulose, talc, highly dispersed silicic acid, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavoring and sweetening agents. For topical administration, the compounds of general formula (I) can also be used in the form of salves and powders; for this purpose, they are mixed with, for example, powdered, physiologically compatible diluents or with conventional salve bases.

The antimicrobial activity of the instantly disclosed compounds was confirmed by the testing of a number of representative or illustrative compounds in certain tests. In one series of tests, the absolute bacteriostatic minimum concentration for each test compound was determined and expressed in micrograms per milliliter. Thus, Table 1 below sets forth, for each test compound, the maximum extent to which the test compound in question can be diluted and still exhibit bacteriostatic activity. As a comparison substance, there was used the commerical bacteriostat known as "Furadantin," which is identified chemically as N-(5-nitrofuryliden)-1-amino-hydantoine. It will be seen from the data presented in Table 1 that the instantly claimed compounds are substantially more active as bacteriostats than the comparison compound, i.e., Furadantin, in that much lower concentrations of the test compounds were capable of acting bacteriostatically, relative to the higher dosages of Furadantin required to achieve this effect. The data for Furadantin are presented at the end of Table 1 infra.

TABLE 1

Absolute Bacteriostatic Minimum Concentrations in μg/ml

| Test Substance [Prep. Ex. No.] | | Escherichia coli (108) | Escherichia coli (106) | Klebsiella pneumoniae (168) |
|---|---|---|---|---|
| 3-(5-Nitro-1-methyl-2-imidazolyl)-6-morpholino-s-triazolo[4,3-b]-pyridazine | [1] | 0.5 | 2 | 0.5 |
| 3-(5-Nitro-1-methyl-2-imidazolyl)-6-dimethylamino-s-triazolo[4,3-b]-pyridazine | [2] | 0.5 | 0.5 | 0.5 |
| 3-(5-Nitro-1-methyl-2-imidazolyl)-6-(4-methyl-piperazine-1-yl)-s-triazolo[4,3-b]pyridazine | [3] | 0.125 | 0.5 | <0.062 |
| 3-(5-Nitro-1-methyl-2-imidazolyl)-6-amino-s-triazolo[4,3-b]pyridazine | [5] | 0.125 | 0.062 | <0.062 |
| N-[3-(5-Nitro-1-methyl-2-imidazolyl)-s-triazolo[4,3-b]pyridazinyl-(6)]-N',N'-dimethyl-formamidine | [6] | 0.125 | 0.25 | 0.5 |
| 3-(1-Methyl-5-nitro-2-imidazolyl)-6-formylamino-s-triazolo[4,3-b]-pyridazine | [7] | 0.125 | 0.125 | 0.5 |
| 3-(5-Nitro-1-methyl-2-imidazolyl)-6-methylamino-s-triazolo[4,3-b]pyridazine | [8] | 0.25 | 0.25 | 0.5 |
| 3-(5-Nitro-1-methyl-2-imidazolyl)-6-(1-piperidinyl-methylen-amino)-s-triazolo[4,3-b]pyridazine | [9] | 0.5 | 1 | 4 |
| 3-(5-Nitro-1-methyl-2-imidazolyl)-6-(morpholino-methylen-amino)-s-triazolo[4,3-b]pyridazine | [10] | 0.25 | 0.5 | 2 |
| 3-(5-Nitro-1-methyl-2-imidazolyl)-6-acetamido-s-triazolo[4,3-b]pyridazine | [11] | 0.031 | 0.125 | 0.25 |
| 3-(5-Nitro-1-methyl-2-imidazolyl)-6-ethylamino-s-triazolo[4,3-b]pyridazine | [12] | 0.25 | 1 | 1 |
| 3-(5-Nitro-1-methyl-2-imidazolyl)-6-(4-methyl-piperazine-1-yl-methylen-amino)-s-triazolo[4,3-b]pyridazine | [13] | 0.25 | 0.5 | 1 |
| 3-(5-Nitro-1-methyl-2-imidazolyl)-6-(aminomethylen-amino)-s-triazolo[4,3-b]pyridazine | [15] | 0.062 | 0.25 | 0.5 |
| 3-(5-Nitro-1-methyl-2-imidazolyl)-6-propionamido-s-triazolo[4,3-b]pyridazine | [16] | 0.062 | 0.125 | 0.25 |
| 3-(5-Nitro-1-methyl-2-imidazolyl)-6-(acetamido-methylenamino)-s-triazolo[4,3-b]pyridazine | [17] | 0.125 | 0.125 | 0.125 |
| 3-(5-Nitro-1-methyl-2-imidazolyl)-6-(diethylamino-methylenamino)-s-triazolo-[4,3-b]pyridazine | [18] | | 0.25 | |
| 3-(5-Nitro-1-methyl-2-imidazolyl)-6-(methylamino-methylenamino)-s-triazolo[4,3-b]pyridazine | [19] | 0.125 | 0.25 | 0.5 |
| 3-(5-Nitro-1-β-hydroxyethyl-2-imidazolyl)-6-methylamino-s-triazolo[4,3-b]pyridazine | [22] | | 1 | |
| 3-(5-Nitro-1-β-acetoxyethyl-2-imidazolyl)-6-(4-methyl-1-piperazinyl)-s-triazolo[4,3-b]pyridazine | [23] | | 2 | |
| 3-(5-Nitro-1-β-hydroxyethyl-2-imidazolyl)-6-(4-methyl-1-piperazinyl)-s-triazolo[4,3-b]pyridazine | [24] | 0.5 | 0.5 | 0.5 |
| 3-(5-Nitro-1-methyl-2-imidazolyl)-6-dimethylsulfimino-s-triazolo[4,3-b]pyridazine | [27] | 0.125 | 0.125 | 0.25 |
| 3-(5-Nitro-1-methyl-2-imidazolyl)-6-(β-hydroxyethylamino-methylenamino)-s-triazolo[4,3-b]pyridazine | [28] | | 0.062 | |
| 1-Methyl-2-[3-(5-Nitro-1-methyl-2-imidazolyl)-6-(s-triazolo[4,3-b]pyridazinyl)-imino]-pyrrolidine | [33] | 0.5 | 1 | 2 |

| Test Substance [Prep. Ex. No.] | | Escherichia Coli (108) | Escherichia coli (106) | Klebsiella pneumonia (168) | Pseudomonas aeruginosa |
|---|---|---|---|---|---|
| 3-(5-Nitro-1-methyl-2-imidazolyl)-s-triazolo[4,3-b]pyridazine | [36] | | 1 | | >64 |
| 3-(5-Nitro-1-methyl-2-imidazolyl)-6-methoxy-s-triazolo[4,3-b]pyridazine | [37] | | 2 | | 32 |
| 3-(5-Nitro-1-methyl-2-imidazolyl)-6-azido-s-triazolo[4,3-b]pyridazine | [38] | | 1 | | 64 |
| 3-(5-Nitro-1-methyl-2-imidazolyl)-6-cyano-s-triazolo[4,3-b]pyridazine | [39] | | 2 | | 128 |
| 3-(5-Nitro-1-methyl-2-imidazolyl)-6-carbamoyl-s-triazolo[4,3-b]pyridazine | [43] | | 0.5 | | 32 |
| 3-(Methyl-2-nitro-5-imidazolyl)-6-dimethylamino-s-triazolo[4,3-b]pyridazine | [47] | 1 | 2 | 4 | |
| 3-(1-Methyl-2-nitro-5-imidazolyl)-6-[N-methyl-N-(β-dimethylaminoethyl)-amino]-s-triazolo[4,3-b]pyridazine | [48] | 0.25 | 1 | 2 | |

TABLE 1-continued

| | Absolute Bacteriostatic Minimum Concentrations in μg/ml | | | |
|---|---|---|---|---|
| Furadantin | 4 | 4 | 8 | <128 |

In another series of tests, the bacteriostatic activity of certain illustrative compounds of this invention in urine was tested and the percentage of administered test substance excreted in the urine was determined, after oral administration, in rats. Again, the comparison substance "Furadantin" (nitrofurantoine) was used in side-by-side comparisons. The results obtained are set forth in Table 2 below, in which the column headed "Maximal Dilution" represents the maximum extent to which a urine sample could be diluted and still exhibit bacteriostatic activity against the test bacterium, which was Escherichia Coli (106). The test compounds were administered at the rate 80 mg (or in the asterisked instances, 20 mg) of test compound per kg of the rat's body weight, and are on the basis of 75 ml of urine per 22 hours after oral administration of the test compound. Each test value is based on the average of values obtained in tests in nine rats and in the instances where two values are set forth, two determinations were made.

The second column in Table 2 below, i.e., the column headed "% of Administered Dosage Excreted," sets forth the amount of test compound excreted in urine, in the above tests, expressed in terms of a percentage of the total amount of compound administered. The corresponding values for the reference standard "Furadantin" are set forth at the bottom of Table 2. It can be seen that the compounds representative of the instant invention were capable of being diluted to a substantially greater extent than Furadantin, and still exhibit bacteriostatic activity; also, most of the compounds of the invention were excreted in urine to a much greater extent than Furadantin.

TABLE 2

Bacteriostatic Activity in Urine and Extent of Excretion in Urine in Rats after Oral Administration

| Test Substance | [Prep. Ex. No] | Minimal Dilution | % of Administered Dosage Excreted |
|---|---|---|---|
| 3-(5-Nitro-1-methyl-2-imidazolyl)-6-morpholino-s-triazolo[4,3-b]pyridazine | [1] | 1:1200 to 1:1500 | 80–100 |
| 3-(5-Nitro-1-methyl-2-imidazolyl)-6-dimethylamino-s-triazolo[4,3-b]pyridazine | [2] | 1:9,000 to 1:10,000 | 100 |
| 3-(5-Nitro-1-methyl-2-imidazolyl)-6-(4-methyl-piperazin-1-yl)-s-triazolo[4,3-b]pyridazine | [3] | 1:2,500 | 20–25 |
| 3-(5-Nitro-1-methyl-2-imidazolyl)-6-amino-s-triazolo[4,3-b]pyridazine | [5] | 1:3,500 | 12.7 |
| N-[3-(5-Nitro-1-methyl-2-imidazolyl)-s-triazolo[4,3-b]pyridazinyl-(6)-N',N'-dimethyl-formamidin | [6] | 1:15,000 | 100 |
| 3-(1-Methyl-5-nitro-2-imidazolyl)-6-formylamino-s-triazolo[4,3-b]-pyridazine | [7] | 1:4,600* | — |
| 3-(5-Nitro-1-methyl-2-imidazolyl)-6-methylamino-s-triazolo[4,3-b]pyridazine | [8] | 1:10,000 | 100* |
| 3-(5-Nitro-1-methyl-2-imidazolyl)-6-(1-piperidinyl-methylenamino-s-triazolo[4,3-b]pyridazine | [9] | 1:9,600 | 42* |
| 3-(5-Nitro-1-methyl-2-imidazolyl)-6-(morpholino-methylen-amino)-s-triazolo[4,3-b]pyridazine | [10] | 1:10,000 | 100* |
| 3-(5-Nitro-1-methyl-2-imidazolyl)-6-acetamido-s-triazolo[4,3-b]pyridazine | [11] | 1:8,900 | 46* |
| 3-(5-Nitro-1-methyl-2-imidazolyl)-6-ethylamino-s-triazolo[4,3-b]pyridazine | [12] | 1:6,100 | — |
| 3-(5-Nitro-1-methyl-2-imidazolyl)-6-(4-methyl-piperazin-1-yl-methylen-amino)-s-triazolo[4,3-b]pyridazine | [13] | 1:10,600 | — |
| 3-(5-Nitro-1-β-acetoxyethyl-2-imidazolyl-6-dimethylamino-s-triazolo[4,3-b]pyridazine | [14]** | 1:600 | — |
| 3-(5-Nitro-1-β-hydroxyethyl-2-imidazolyl)-6-dimethylamino-s-triazolo[4,3-b]pyridazine | [14] | 1:880 | — |
| 3-(5-Nitro-1-methyl-2-imidazolyl)-6-(aminomethylen-amino)-s-triazolo[4,3-b]pyridazine | [15] | 1:13,000 | 47* |
| 3-(5-Nitro-1-methyl-2-imidazolyl)-6-propionamido-s-triazolo[4,3-b]pyridazine | [16] | 1:8,000 | 68* |
| 3-(5-Nitro-1-methyl-2-imidazolyl)-6-dimethylsulfimino-s-triazolo[4,3-b]pyridazine | [27] | < 1:1,000 | |
| 3-(5-Nitro-1-methyl-2-imidazolyl)-6-(β-hydroxyethylamino-methylenamino)-s-triazolo[4,3-b]pyridazine | [28] | 1:11,900 | 45* |
| 1-Methyl-2-[3-(5-Nitro-1-methyl-2-imidazolyl)-6-(s-triazolo-[4,3-b]pyridazinyl-imino]-pyrrolidine | [33] | 1:3,700 | |
| N-[3-(5-Nitro-1-methyl-2-imidazolyl)-s-triazolo[4,3-b]-pyridazine-6yl]N'-diathyl-acetamidine | [34] | < 1:1,000 | |
| 3-(5-Nitro-1-methyl-2-imidazolyl)-6-azido-s-triazolo[4,3-b]pyridazine | [38] | < 1:1,000 | |
| 3-(5-Nitro-1-methyl-2-imidazolyl)-6-carbamoyl-s-triazolo[4,3-b]pyridazine | [43] | 1:400 | |
| 3-(5-Nitro-1-methyl-2-imidazolyl)-6-(N-n-butyl-carbamoyl)-s-triazolo[4,3-b]pyridazine | [44] | 1:60* | |
| 3-(1-Methyl-2-nitro-5-imidazolyl)-6-[N-methyl-N-(β-dimethylaminoethyl)-amino]-s-triazolo[4,3-b]pyridazine | [48] | 1:400 | |
| 3-(1-Methyl-2-nitro-5-imidazolyl)-6-(dimethylamino-methylenamino)-s-triazolo[4,3-b]pyridazine | [50] | < 1:138 | 27* |
| 3-(5-Nitro-1-methyl-2-imidazolyl)-6-(acetamido-methylenamino)-s-triazolo[4,3-b]pyridazine | [17] | 1:1000 | |

TABLE 2-continued

Bacteriostatic Activity in Urine and Extent of Excretion in Urine in Rats after Oral Administration

| Test Substance | [Prep. Ex. No] | Minimal Dilution | % of Administered Dosage Excreted |
|---|---|---|---|
| 3-(5-Nitro-1-methyl-2-imidazolyl)-6-diethylamino-methylenamino)-s-triazolo[4,3-b]pyridazine | [18] | 1:10,900 1:1,730* | 100* |
| 3-(5-Nitro-1-methyl-2-imidazolyl)-6-(methylamino-methylenamino)-s-triazolo[4,3-b]pyridazine | [19] | 1:11,000 | 70* |
| 3-(5-Nitro-1-methyl-2-imidazolyl)-6-piperidino-s-triazolo[4,3-b]pyridazine | [20] | 1:970 | 100* |
| 3-(5-Nitro-1-β-hydroxyethyl-2-imidazolyl)-6-methylamino-s-triazolo[4,3-b]pyridazine | [22] | 1:155 | 16 |
| 3-(5-Nitro-1-β-acetoxyethyl-2-imidazolyl)-6-(4-methyl-1-piperazinyl)-s-triazolo[4,3-b]pyridazine | [23] | < 1:1,000 | 39* |
| 3-(5-Nitro-1-β-hydroxyethyl-2-imidazolyl)-6-(4-methyl-1-piperazinyl)-s-triazolo[4,3-b]pyridazine | [24] | 1:180* | 24* |
| 3-(5-Nitro-1-ethyl-2-imidazolyl)-6-dimethylamino-s-triazolo[4,3-b]pyridazine | [25] | 1:755 | |
| Furadantin | | 1:20 to 1:59 | 27–46 |

**precursor of Ex. 14 title compound

In yet an additional series of tests, the trichomonacidal activity of certain of the compounds of the invention in vitro was determined, against two Trichomonas species, expressed in the minimum concentration, in micrograms per milliliter, needed to exhibit trichomonacidal action. In these series of tests, the results of which are set forth in Table 3 below, the comparison substance was "Flagyl," which is chemically identified as 1-(2'-hydroxyethyl)-2-methyl-5-nitro-imidazole. It can be seen from the data in Table 3 that the instant compounds were trichomonacidally active at lower concentrations than the comparison material with respect to one Trichomonas species and that three out of the four test compounds of the invention were active at lower concentrations than "Flagyl" against the second Trichomonas species.

The compounds of this invention can thus be described as anti-parasiticides with specific activity against Trichomonas vaginalis, as well as Lamblia intestinales and Entamoeba histolitica, and the materials of the invention are active not only locally, but per os.

In general, the compounds of the invention exhibit similar activity, but, in most instances, to a greater degree, as the commercial material known as "Flagyl," marketed by Etablissements R. Barberot S.A., Geneva, Switzerland.

It will be understood that the specification and examples are illustrative but not limitative of the present invention and that other embodiments within the spirit and scope of the invention will suggest themselves to those skilled in the art.

What is claimed is:

TABLE 3

Trichomonacidal Activity in Vitro

| Test Compound | | Trichomonacidal Minimal Concentration in μg/ml. | |
|---|---|---|---|
| | | Trichomonas vaginalis Carneri | Trichomonas vaginalis Samuels |
| 3-(5-Nitro-1-methyl-2-imidazolyl)-6-dimethylamino-s-triazolo[4,3-b]pyridazine | [2] | 0.25 | 0.5 |
| 3-(5-Nitro-1-methyl-2-imidazolyl)-6-(4-methyl-piperazin-1-yl)-s-triazolo[4,3-b]pyridazine | [3] | 0.062 | 0.125 |
| 3-(5-Nitro-1-methyl-2-imidazolyl)-6-amino-s-triazolo[4,3-b]pyridazine | [5] | 1 | 2 |
| N-[3-(5-Nitro-1-methyl-2-imidazolyl)-s-triazolo[4,3-b]pyridazinyl-(6)]-N',N-dimethyl-formamidin | [6] | 0.5 | 0.5 |
| "Flagyl" [1-(2'-hydroxyethyl)-2-methyl-5-nitro-imidazolo] | | 2 | 1 |

The particular mode of administration and dosage of inventive compound to be applied in treating a given bacterial infection or infirmity will, of course, be determined by the physician, taking into account all the circumstances of a particular case. However, in general, tablets containing the test compound to be administered per os, will contain about 250 mg of active material and, for local administration, may contain about 500 mg of active substance. The dosage to be applied may be one tablet taken in the morning and in the evening with the corresponding meal, for, e.g. ten consecutive days, if the compound is applied per os. For local administration, one ovule may be applied for 10 to 20 days every evening. In men, the per os administration may have to be increased to, e.g., 750 mg to 1 g, instead of the standard 250 mg per tablet dosage.

1. A method of combating a bacterial infection in a mammal which comprises administering to such mammal an antibacterially effective amount of a nitroimidazolyl-triazolo-pyridazine compound of the formula

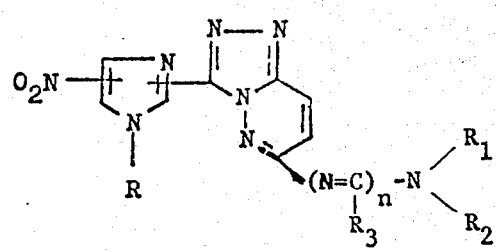

wherein
R is hydrogen, lower alkyl, 2-hydroxyl-alkyl, 2-alkanoyloxyalkyl, or 2-alkoxyalkyl, wherein the alkyl moieties contain up to 6 carbon atoms;
$R_1$ and $R_2$ are, individually, hydrogen, lower alkanoyl, aroyl, alkoxycarbonyl, alkyl, cycloalkyl, wherein the alkyl or cycloalkyl radicals may contain a hydroxyl, alkoxy or amino group or an alkyl-, alkanoyl- or aroyl- amino group;
$R_1$ and $R_2$, taken together, represent with the N-atom piperidino, hydroxy-piperidino, alkyl-piperidino, piperazino, alkyl-piperazino or morpholino;
$R_1$ and $R_2$, taken together, can also represent dialkylsulfimino or dialkylsulfoximino;
$R_3$ is hydrogen or alkyl; or
$R_3$, together with $R_2$, represents an alkylene bridge of from 3 to 4 carbon atoms; wherein the alkyl groups or moieties contained in the $R_1$, $R_2$ and $R_3$ radicals are of from 1 to 6 carbon atoms in each instance, the aryl groups or moieties are of 6 carbon atoms and the cycloalkyl groups or moieties are of 3 to 8 carbon atoms; and
$n$ is 0 to 1; or a pharmacologically acceptable salt thereof.

2. The method as claimed in claim 1, wherein R is hydrogen.

3. The method as claimed in claim 1, wherein R is alkyl, 2-hydroxyalkyl, 2-alkanoyloxyalkyl, or 2-alkoxyalkyl.

4. The method as claimed in claim 1, wherein the nitroimidazolyl moiety shown in said formula is 5-nitro-2-imidazoyl.

5. The method as claimed in claim 1, wherein the nitroimidazolyl moiety in said formula is 2-nitro-5-imidazoyl.

6. The method as claimed in claim 1, wherein said pyridazine compound is 3-(5-nitro-1-methyl-2-imidazolyl)-6-dimethylamino-s-triazolo[4,3-b]pyridazine.

7. The method as claimed in claim 1, wherein said pyridazine compound is 3-(5-nitro-1-methyl-2-imidazolyl)-6-(4-methylpiperazin-1-yl)-s-triazolo[4,3-b]pyridazine.

8. The method as claimed in claim 1, wherein said pyridazine compound is 3-(5-nitro-1-methyl-2-imidazolyl)-6-amino-s-triazolo-[4,3-b]pyridazine.

9. The method as claimed in claim 1, wherein said pyridazine compound is N-[3-(5-nitro-1-methyl-2-imidazolyl)-s-triazolo[4,3-b]-pyridazin-6-yl]-N',-N'dimethylformamidine.

10. The method as claimed in claim 1, wherein said pyridazine compound is 3-(5-nitro-1-methyl-2-imidazolyl)-6-(aminomethylene-amino)-s-triazolo[4,3-b]pyridazine.

11. The method as claimed in claim 1, wherein said pyridazine compound is administered locally.

12. The method as claimed in claim 1, wherein said pyridazine compound is administered per os.

13. The method as claimed in claim 1, wherein the dosage of said pyridazine compound administered is from 5 to 50 mg per kg of bodyweight of said mammal.

14. An antibacterial composition comprising a pharmaceutically acceptable carrier and an antibacterially effective amount of a nitroimidazolyl-triazolo-pyridazine compound of the formula

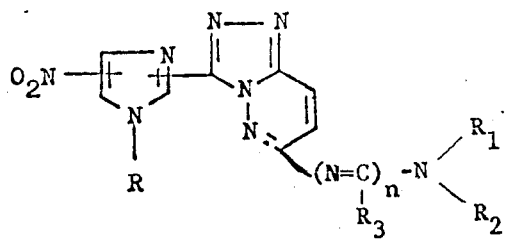

wherein
R is hydrogen, lower alkyl, 2-hydroxyl-alkyl, 2-alkanoyloxyalkyl, or 2-alkoxyalkyl, wherein the alkyl moieties contain up to 6 carbon atoms;
$R_1$ and $R_2$ are, individually, hydrogen, lower alkanoyl, aroyl, alkoxycarbonyl, alkyl, cycloalkyl, wherein the alkyl or cycloalkyl radicals may contain a hydroxyl, alkoxy or amino group or an alkyl-, alkanoyl- or aroyl- amino group;
$R_1$ and $R_2$, taken together, represent with the N-atom piperidino, hydroxy-piperidino, alkyl-piperidino, piperazino, alkyl-piperazino or morpholino;
$R_1$ and $R_2$, taken together, can also represent dialkylsulfimino or dialkylsulfoximino;
$R_3$ is hydrogen or alkyl; or
$R_3$, together with $R_2$, represents an alkylene bridge of from 3 to 4 carbon atoms; wherein the alkyl groups or moieties contained in the $R_1$, $R_2$ and $R_3$ radicals are of from 1 to 6 carbon atoms in each instance, the aryl groups or moieties are of 6 carbon atoms and the cycloalkyl groups or moieties are of 3 to 8 carbon atoms; and
$n$ is 0 to 1;
or a pharmacologically acceptable salt thereof.

15. The composition as claimed in claim 14, wherein said pyridazine compound is selected from the group consisting of
3-(5-nitro-1-methyl-2-imidazolyl)-6-dimethylamino-s-triazolo[4,3-b]pyridazine
3-(5-nitro-1-methyl-2-imidazolyl)-6-(4-methylpiperazin-1-yl)-s-triazolo[4,3-b]pyridazine
3-(5-nitro-1-methyl-2-imidazolyl)-6-amino-s-triazolo-[4,3-b]pyridazine
N-[3-(5-nitro-1-methyl-2-imidazolyl)-s-triazolo[4,3-b]pyridazin-6-yl]-N',N'dimethylformamidine
and
3-(5-nitro-1-methyl-2-imidazolyl)-6-(aminomethylene-amino)-s-triazolo[r,3-b]pyridazine

* * * * *